(12) United States Patent
Kim et al.

(10) Patent No.: US 12,415,891 B2
(45) Date of Patent: Sep. 16, 2025

(54) AMPHIPHILIC POLY (AMINO ACID), BLOCK COPOLYER USING THE AMPHIPHILIC POLY (AMINO ACID), AND COMPLEX INCLUDING THE AMPHIPHILIC POLY (AMINO ACID) OR THE BLOCK COPOLYMER AND NUCLEIC ACID

(71) Applicant: The University of Tokyo, Tokyo (JP)

(72) Inventors: HyunJin Kim, Tokyo (JP); Kanjiro Miyata, Tokyo (JP); Kazunori Kataoka, Tokyo (JP)

(73) Assignee: The University of Tokyo (JP)

( * ) Notice: Subject to any disclaimer, the term of this patent is extended or adjusted under 35 U.S.C. 154(b) by 724 days.

(21) Appl. No.: 17/280,058

(22) PCT Filed: Sep. 25, 2019

(86) PCT No.: PCT/JP2019/037555
§ 371 (c)(1),
(2) Date: Mar. 25, 2021

(87) PCT Pub. No.: WO2020/067142
PCT Pub. Date: Apr. 2, 2020

(65) Prior Publication Data
US 2021/0340322 A1    Nov. 4, 2021

(30) Foreign Application Priority Data

Sep. 25, 2018    (JP) .................................. 2018-178320

(51) Int. Cl.
| C08G 69/10 | (2006.01) |
| A61K 31/7105 | (2006.01) |
| A61K 47/64 | (2017.01) |
| C08F 293/00 | (2006.01) |
| C08L 77/04 | (2006.01) |
| C12N 15/87 | (2006.01) |

(52) U.S. Cl.
CPC .......... C08G 69/10 (2013.01); A61K 31/7105 (2013.01); A61K 47/6455 (2017.08); C08F 293/00 (2013.01); C08L 77/04 (2013.01); C12N 15/87 (2013.01)

(58) Field of Classification Search
CPC ............... C08G 69/10; A61K 47/6455; A61K 31/7105; C08F 293/00; C08L 77/04; C12N 15/87
See application file for complete search history.

(56) References Cited

U.S. PATENT DOCUMENTS

| 5,858,278 A | 1/1999 | Itoh et al. |
| 7,557,110 B2 | 7/2009 | Kataoka et al. |
| 7,719,796 B2 | 5/2010 | Takahashi et al. |
| 7,780,957 B2 | 8/2010 | Kataoka et al. |
| 7,829,657 B2 | 11/2010 | Kataoka et al. |
| 8,318,205 B2 | 11/2012 | Kataoka et al. |
| 8,450,282 B2 | 5/2013 | Kataoka et al. |
| 8,546,487 B2 | 10/2013 | Kataoka et al. |
| 8,592,385 B2 | 11/2013 | Kataoka et al. |
| 8,791,086 B2 | 7/2014 | Kataoka et al. |
| 8,853,167 B2 | 10/2014 | Kato et al. |
| 8,906,503 B2 | 12/2014 | Kataoka et al. |
| 9,051,354 B2 | 6/2015 | Kataoka et al. |
| 9,114,177 B2 | 8/2015 | Kataoka et al. |
| 9,278,075 B2 | 3/2016 | Kataoka et al. |
| 9,303,122 B2 | 4/2016 | Kataoka et al. |
| 9,314,529 B2 | 4/2016 | Kataoka et al. |
| 9,750,687 B2 | 9/2017 | Kataoka et al. |
| 9,782,358 B2 | 10/2017 | Kataoka et al. |
| 12,116,458 B2 | 10/2024 | Lee et al. |
| 2006/0189632 A1 | 8/2006 | Katanoka et al. |
| 2007/0002494 A1 | 1/2007 | Takahashi et al. |

(Continued)

FOREIGN PATENT DOCUMENTS

| CN | 112334510 A | 2/2021 |
| EA | 016911 B1 | 8/2012 |

(Continued)

OTHER PUBLICATIONS

K. Miyata et al., "Polyplexes from Poly (aspartamide) Bearing 1,2-Diaminoethane Side Chains Induce pH-Selective, Endosomal Membrane Destabilization with Amplified Transfection and Negligible Cytotoxicity," *J. Am. Chem. Soc.*, 130, 16287-16294 (2008).

(Continued)

*Primary Examiner* — Li N Komatsu

(74) *Attorney, Agent, or Firm* — Leydig, Voit & Mayer, Ltd.

(57) ABSTRACT

An amphiphilic poly(amino acid) for nucleic acid delivery, which is represented by the following formula (1):

[Chem. 1]

$$R^1-(COCHNH)_{m-n}-(COR^{3b}CHNH)_n-(COCHNH)_{x-y-z}- \atop {\overset{|}{R^{3a}}} \quad {\overset{|}{C=O}} \quad {\overset{|}{R^{4a}}} \atop {\overset{|}{C=O}} \quad {\overset{|}{R^{5b}}} \quad {\overset{|}{C=O}} \atop {\overset{|}{R^{5a}}} \quad {\overset{|}{R^{6b}}} \quad {\overset{|}{R^{7a}}} \atop {\overset{|}{R^{6a}}}$$

(1)

$$-(COR^{4b}CHNH)_y-(COCHNH)_z-R^2. \atop {\overset{|}{C=O}} \quad {\overset{|}{R^8}} \atop {\overset{|}{R^{7b}}}$$

16 Claims, 6 Drawing Sheets

(56) References Cited

U.S. PATENT DOCUMENTS

| | | |
|---|---|---|
| 2007/0059271 A1 | 3/2007 | Kataoka et al. |
| 2008/0249049 A1 | 10/2008 | Kataoka et al. |
| 2009/0258416 A1 | 10/2009 | Kataoka et al. |
| 2010/0137512 A1 | 6/2010 | Kataoka et al. |
| 2011/0060123 A1 | 3/2011 | Kataoka et al. |
| 2011/0256227 A1 | 10/2011 | Mirosevich et al. |
| 2012/0046453 A1 | 2/2012 | Kataoka et al. |
| 2012/0053295 A1 | 3/2012 | Kataoka et al. |
| 2012/0064346 A1 | 3/2012 | Kataoka et al. |
| 2012/0149649 A1 | 6/2012 | Kato et al. |
| 2012/0177594 A1 | 7/2012 | Kataoka et al. |
| 2012/0196810 A1 | 8/2012 | Kataoka et al. |
| 2012/0237565 A1 | 9/2012 | Mirosevich et al. |
| 2013/0109743 A1 | 5/2013 | Kataoka et al. |
| 2013/0202711 A1 | 8/2013 | Kataoka et al. |
| 2014/0017328 A1 | 1/2014 | Kataoka et al. |
| 2015/0051347 A1 | 2/2015 | Kataoka et al. |
| 2015/0141575 A1 | 5/2015 | Kataoka et al. |
| 2016/0051484 A1 | 2/2016 | Kataoka et al. |
| 2016/0106855 A1 | 4/2016 | Ziv |
| 2016/0184457 A1 | 6/2016 | Kataoka et al. |
| 2016/0230189 A1 | 8/2016 | Kotha et al. |
| 2017/0173182 A1 | 6/2017 | Kataoka et al. |
| 2017/0183389 A1 | 6/2017 | Itaka et al. |
| 2018/0185281 A1 | 7/2018 | Kataoka et al. |
| 2021/0238347 A1 | 8/2021 | Lee et al. |
| 2021/0340322 A1 | 11/2021 | Kim et al. |
| 2022/0340711 A1 | 10/2022 | Lee et al. |
| 2022/0340712 A1 | 10/2022 | Lee et al. |
| 2023/0147779 A1 | 5/2023 | Lee et al. |
| 2024/0285781 A1 | 8/2024 | Lee et al. |

FOREIGN PATENT DOCUMENTS

| | | |
|---|---|---|
| EP | 2397487 A1 | 12/2011 |
| EP | 2399948 A1 | 12/2011 |
| JP | 2003-505473 A | 2/2003 |
| JP | 2010-285460 A | 12/2010 |
| JP | 2011-026219 A | 2/2011 |
| JP | 2011-173802 A | 9/2011 |
| WO | WO 1999/061512 A1 | 12/1999 |
| WO | WO 2000/067142 A1 | 11/2000 |
| WO | WO 2001/007486 A1 | 2/2001 |
| WO | WO 2006/085664 A1 | 8/2006 |
| WO | WO 2007/099660 A1 | 9/2007 |
| WO | WO 2010/093036 A1 | 8/2010 |
| WO | WO 2011/105402 A1 | 1/2011 |
| WO | WO 2017/053312 A1 | 3/2017 |
| WO | WO 2017/056095 A1 | 4/2017 |
| WO | WO 2017/002979 A1 | 5/2017 |
| WO | WO 2017/192512 A2 | 9/2017 |
| WO | WO 2018/053795 A1 | 3/2018 |
| WO | WO 2018/094356 A2 | 5/2018 |
| WO | WO 2019/210326 A2 | 12/2019 |
| WO | WO 2020/086910 A1 | 4/2020 |
| WO | WO 2020/219776 A1 | 10/2020 |
| WO | WO 2020/243370 A1 | 12/2020 |
| WO | WO 2021/217082 A1 | 10/2021 |
| WO | WO 2022/261561 A1 | 12/2022 |

OTHER PUBLICATIONS

International Search Report, issued in corresponding International application No. PCT/JP2019/037555 dated Dec. 24, 2019.

Extended European Search Report issued in EP Application No. 19867266.9, dated Sep. 12, 2022.

Hyun Jin Kim et al., "Introduction of stearoyl moieties into a biocompatible cationic polyaspartamide derivative, PAsp(DET), with endosomal escaping function for enhanced siRNA-mediated gene knockdown," Journal of Controlled Release 145 (2), pp. 141-148 (2010).

Hyun Jin Kim et al., "Fine-Tuning of Hydrophobicity in Amphiphilic Polyaspartamide Derivatives for Rapid and Transient Expression of Messenger RNA Directed Toward Genome Engineering in Brain," ACS Central Science, vol. 5, No. 11, pp. 1866-1875 (2019).

Jongmin Yum et al., "Fine-tuning of polyaspartamide derivatives with alicyclic moieties for systemic mRNA delivery," Journal of Controlled Release, vol. 342 (4), pp. 148-156 (2022).

Foster, Suzanne et al., "Intracellular Delivery of a Protein Antigen with an Endosomal-Releasing Polymer Enhances CD8 T-Cell Production and Prophylactic Vaccine Efficacy," Bioconjug Chem, 21(12) pp. 2205-2212 (2010).

Fu, Ailing et al., "Promises and Pitfalls of Intracellular Delivery of Proteins," Bioconjugate Chemistry, 25, pp. 1602-1608 (2014).

Lackey, Chantal A. et al., "A biomimetic pH-Responsive Polymer Directs Endosomal Release and Intracellular Delivery of an Endocytosed Antibody Complex," Bioconjugate Chemistry, 13 (5), pp. 996-1001 (2002) (abstract only).

Liu C. et al., "Novel biodegradable lipid nano complex for siRNA delivery significantly improving the chemosensitivity of human colon cancer stem cells to paclitaxel," Journal of Controlled Release, Elsevier, Amsterdam, NL, vol. 140, No. 3, pp. 277-283 (2009).

Maier, Kevin et al., "Acid-Labile Traceless Click Linker for Protein Transduction," Journal of the American Chemical Society, 134, pp. 10169-10173 (2012).

Nauka, PC et al., "Enhancing Conjugation Yield of Brush Polymer-Protein Conjugates by Increasing Linker Length at the Polymer End-Group," Polym Chem, 7 (13), pp. 2352-2357 (2016).

Qi, Yizhi et al., "Protein-Polymer Conjungation-Moving Beyond PEGylation," Curr Opin Chem Biol, 28, pp. 181-193 (2015).

Rozema, David B. et al., "Endosomolysis by Masking of a Membrane-Active Agent (EMMA) for Cytoplasmic Release of Macromolecules," Bioconjugate Chem, 14, pp. 51-57 (2003).

Song et al., "Synthetic polypeptides: from polymer design to supramolecular assembly and biomedical application," Chem. Soc Rev., 25, vol. 46, No. 21, pp. 6570-6599 (2017).

Takemoto, Hiroyasu et al., "Acid pH-Responsive siRNA Conjugate for Reversible Carrier Stability and Accelerated Endosomal Escape with Reduced IFNα-Associated Immune Response", Angew. Chem. Int. Ed, 52, pp. 6218-6221 2013.

Tangsangasaksri, Montira et al., "siRNA-Loaded Polyion Complex Micelle Decorated with Charge-Conversional Polymer Tuned to Undergo Stepwise Response to Intra-Tumoral and Intra-Endosomal pHs for Exerting Enhanced RNAi Efficacy," BioMacromolecules, 17, pp. 246-255 (2016).

Tian, Li et al., "Endosomolytic reducible polymeric electrolytes for cytosolic protein delivery," Biomacromolecules, 14(8), pp. 2570-2581 (2013).

Uchida, Hirokuni et al., "Modulated Protonation of Side Chain Aminoethylene Repeats in N-Substituted Polyaspartamides Promotes mRNA Transfection," Journal of the American Chemical Society, 136, pp. 12396-12405 (2014).

Van Dijk-Wolthuis, WN et al., "A versatile method for the conjugation of proteins and peptides to poly[2-(dimethylamino)ethyl methacrylate]," Bioconjug Chem, 10(4), pp. 687-692 (1999) (abstract only).

[Fig. 1]
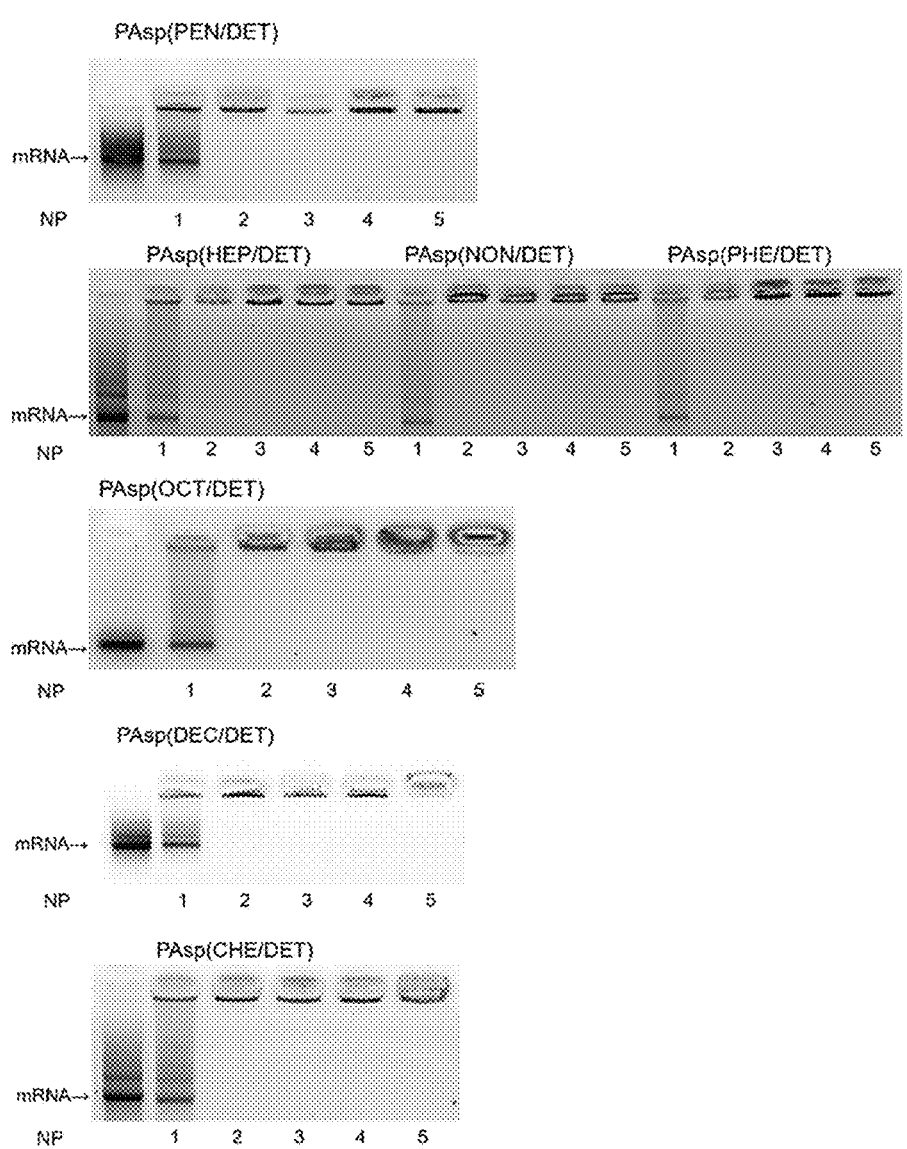
[Fig. 2]
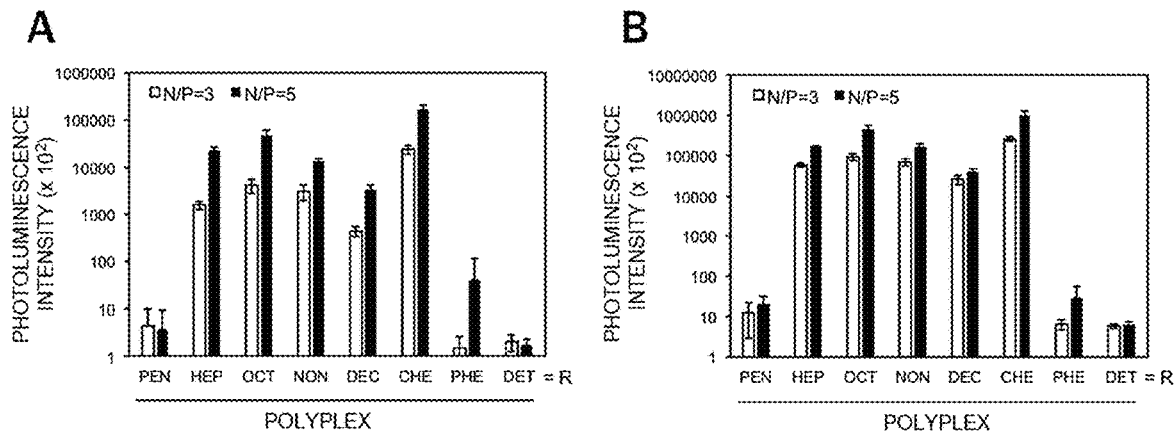

[Fig. 3-1]
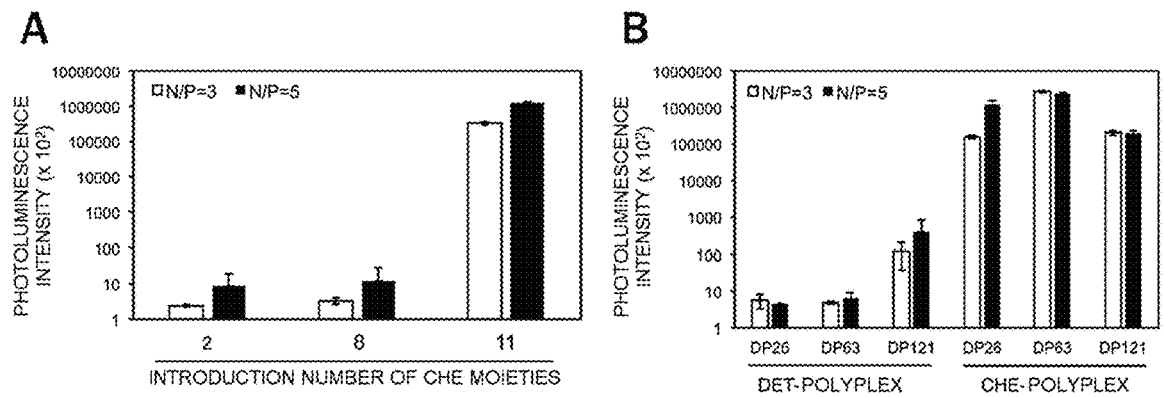
[Fig. 3-2]
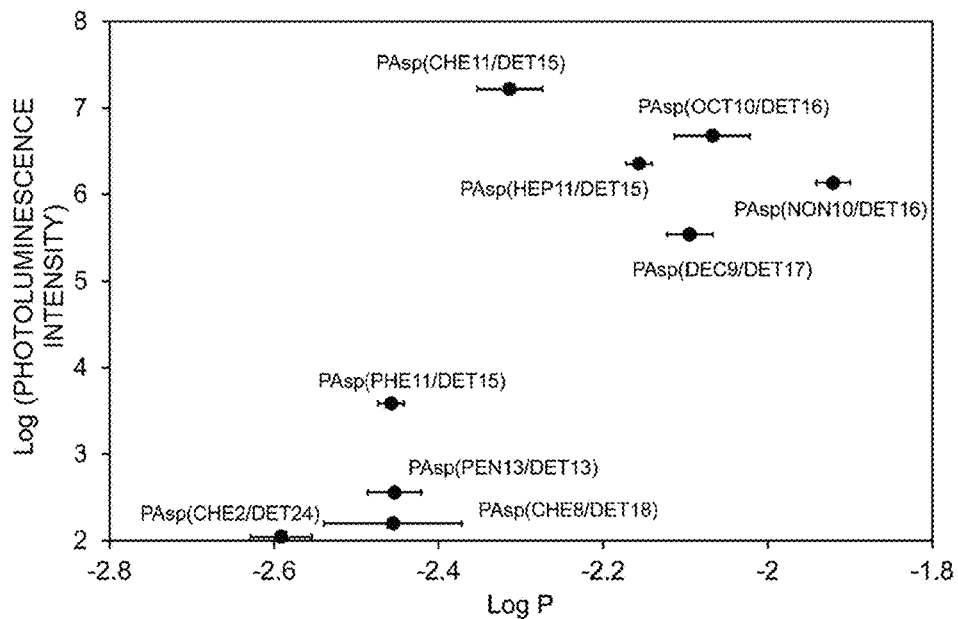
[Fig. 4]
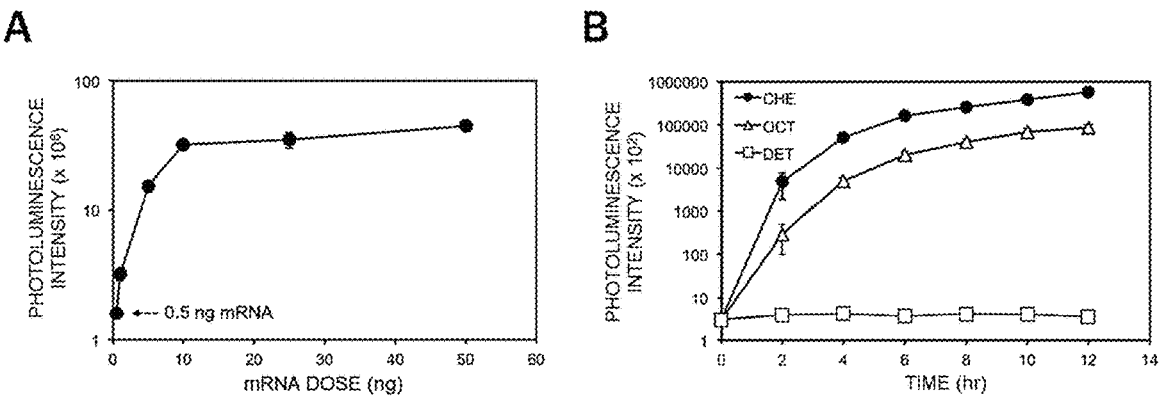

[Fig. 5]
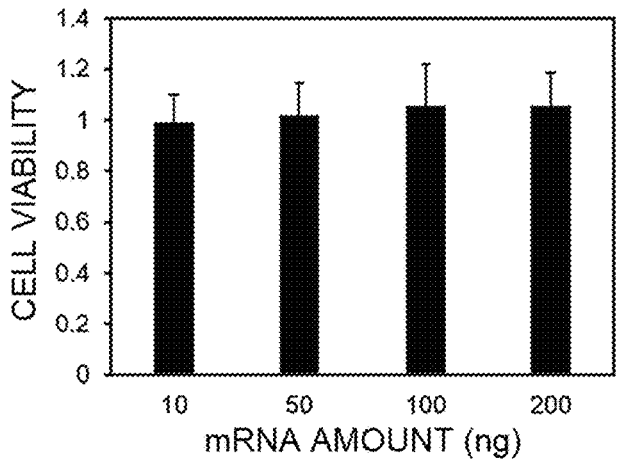
[Fig. 6]
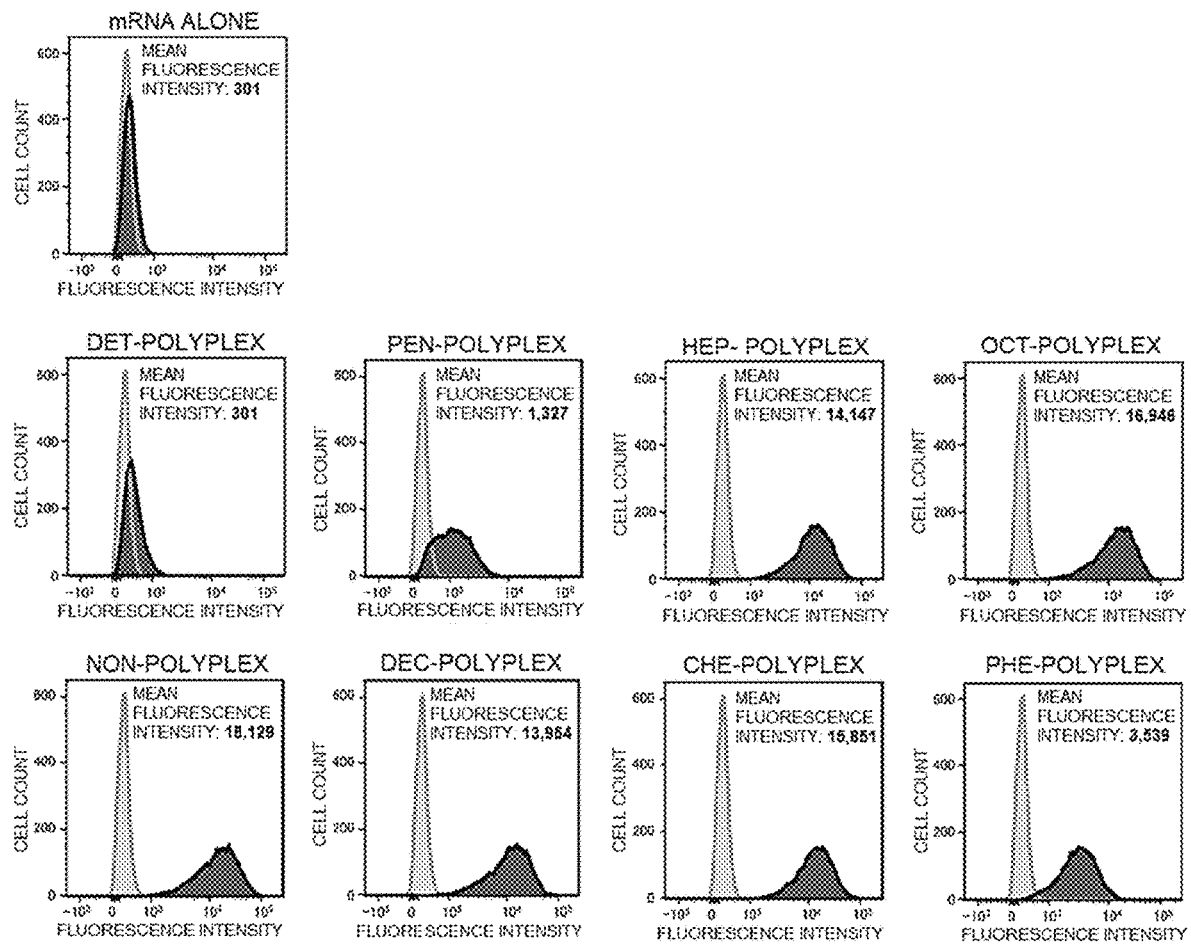

[Fig. 7]
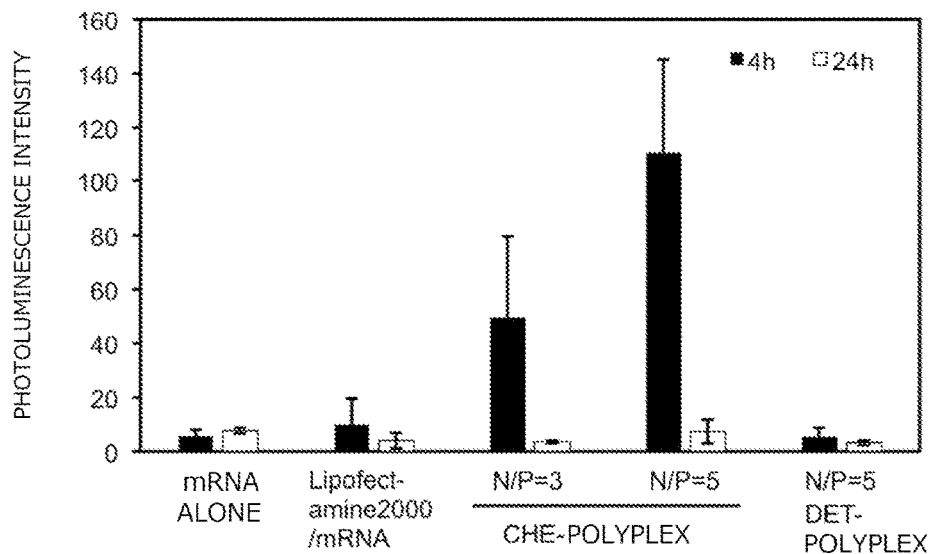
[Fig. 8]
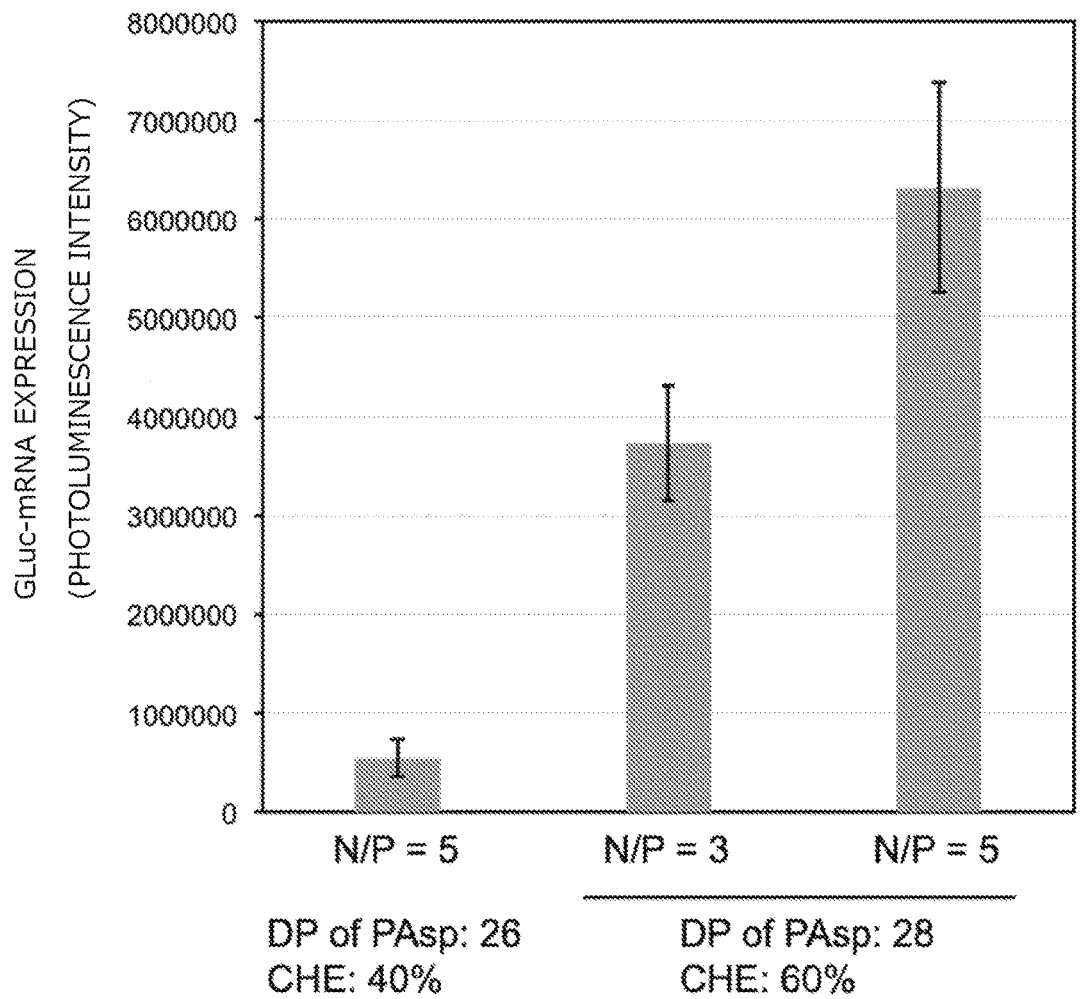

[Fig. 9]
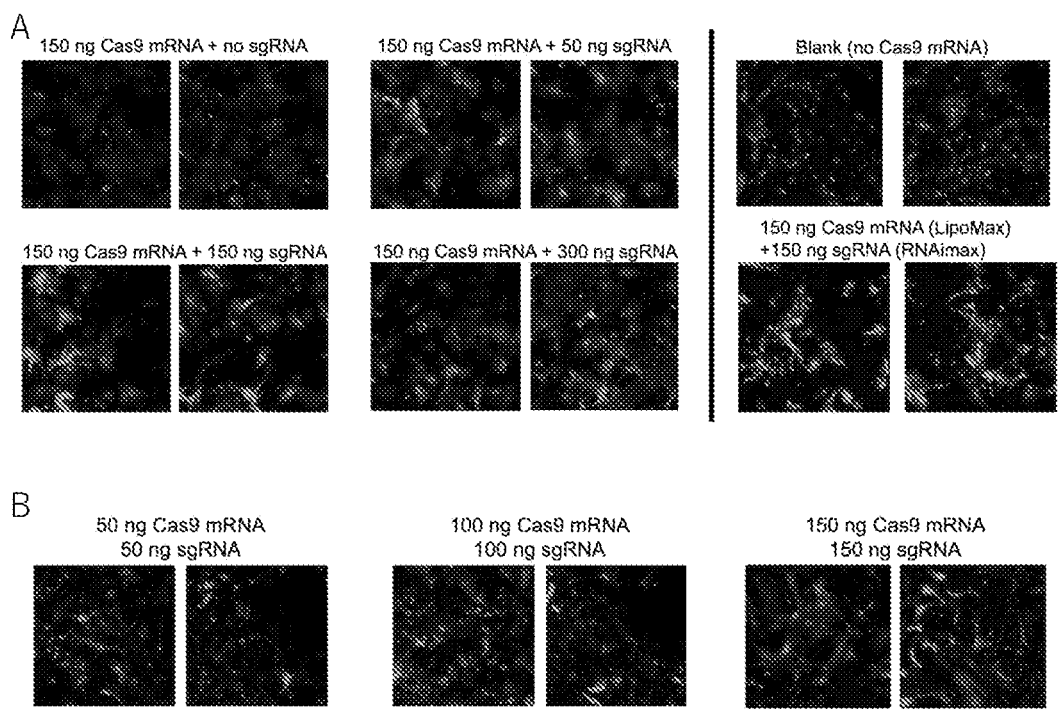
[Fig. 10]
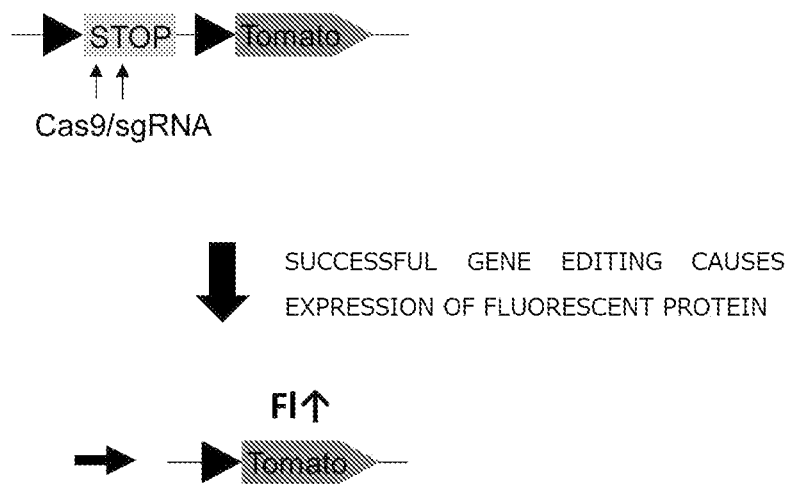
SUCCESSFUL GENE EDITING CAUSES EXPRESSION OF FLUORESCENT PROTEIN

[Fig. 11]
(a) (b)
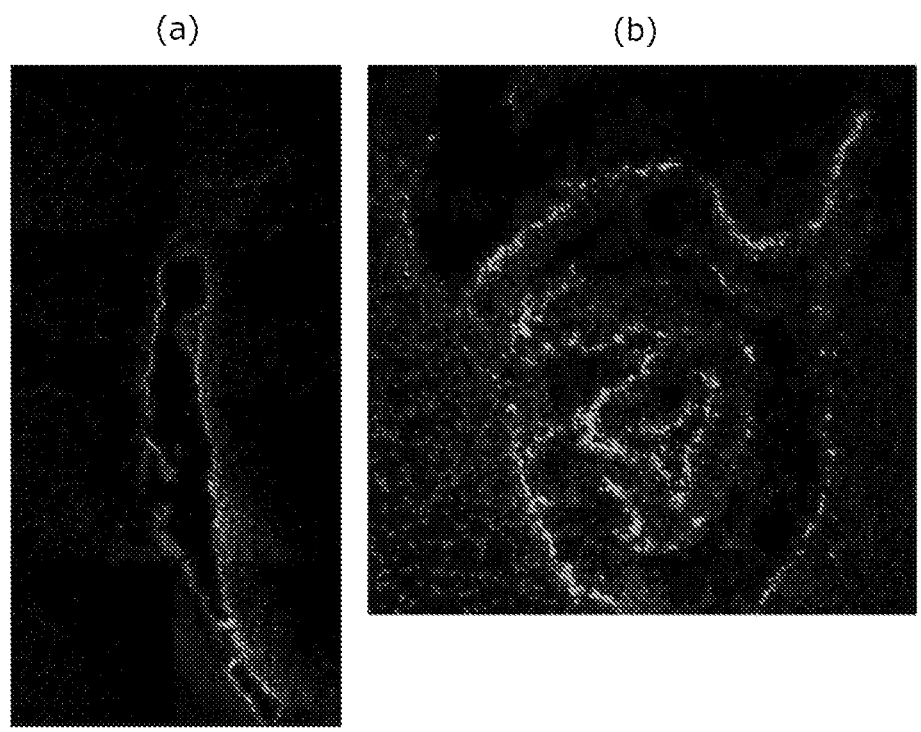
[Fig. 12]
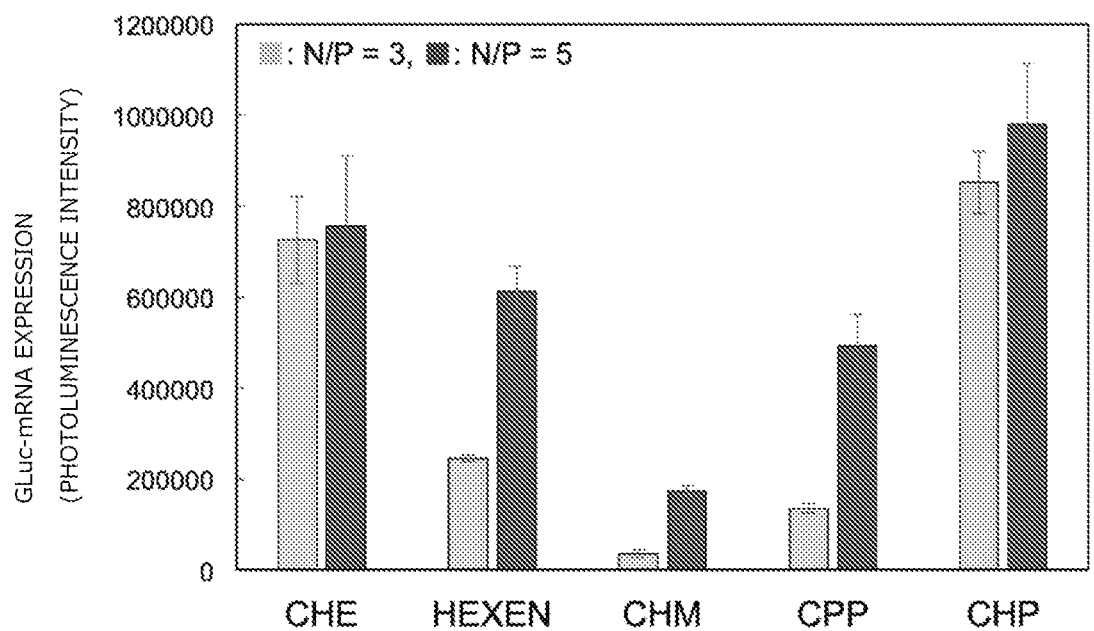

AMPHIPHILIC POLY (AMINO ACID), BLOCK COPOLYER USING THE AMPHIPHILIC POLY (AMINO ACID), AND COMPLEX INCLUDING THE AMPHIPHILIC POLY (AMINO ACID) OR THE BLOCK COPOLYMER AND NUCLEIC ACID

TECHNICAL FIELD

The present invention relates to an amphiphilic poly (amino acid), a block copolymer using the amphiphilic poly(amino acid), and a complex including the amphiphilic poly(amino acid) or the block copolymer and a nucleic acid.

BACKGROUND ART

In recent years, rapid development has been made for nucleic acid therapeutics, such as an antisense nucleic acid and small interfering RNA (siRNA), gene therapeutics formed of nucleic acids encoding genes for therapeutic proteins, such as plasmid DNA and messenger RNA (mRNA), genome editing technology using single guide RNA (sgRNA) and Cas9 nuclease, and the like. Along with this, there has been a demand for development of a carrier to introduce a nucleic acid accurately into cells.

Carriers to introduce nucleic acids into cells are broadly classified into a viral vector and a nonviral carrier. The nonviral carrier has advantages of, for example, being free of immunogenicity and being easy to prepare and handle.

Specific examples of the nonviral carrier include: a cationic lipid, such as a LIPOFECTAMINE™ series; and a cationic poly(amino acid) containing a cationic group in a side chain thereof. Those carriers can form complexes with nucleic acids (a lipoplex and a polyplex, respectively) and introduce them into cells via endocytosis.

Examples of the cationic poly(amino acid) include poly (N-[N-(2-aminoethyl)-2-aminoethyl]aspartamide) (PAsp (DET)) having an ethylenediamine structure in a side chain thereof and a block copolymer containing the PAsp(DET) as one block component thereof. It has been confirmed that those cationic poly(amino acid)s form polyplexes with plasmid DNA and introduce the plasmid DNA into cells with high efficiency, to thereby express a gene encoded in the plasmid DNA (see Non Patent Literature 1, Patent Literature 1, and Patent Literature 2).

As described above, the PAsp(DET) and the block copolymer containing the PAsp(DET) as one block component thereof are each effective as a carrier for introducing plasmid DNA into cells, but are not satisfactory regarding mRNA introduction.

CITATION LIST

Patent Literature

PTL 1: WO 2006/085664 A1
PTL 2: WO 2007/099660 A1

Non Patent Literature

NPL 1: K. Miyata et al., J. Am. Chem. Soc. 2008, 130, 16287-16294

SUMMARY OF INVENTION

Technical Problem

The present invention has been made in order to solve the problem of the related techniques described above, and a primary object of the present invention is to provide a nonviral carrier capable of suitably introducing nucleic acids including mRNA into cells.

Solution to Problem

According to one embodiment of the present invention, there is provided an amphiphilic poly(amino acid) for nucleic acid delivery, which is represented by the following formula (1):

[Chem. 1]

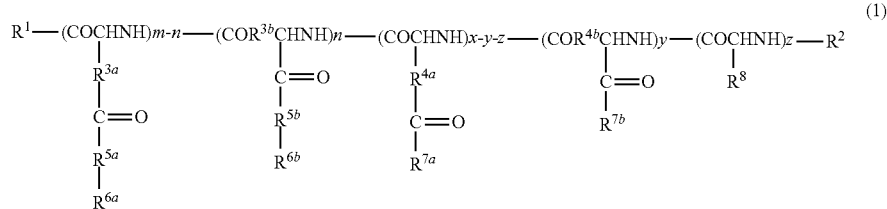

(1)

where:
R$^1$ represents a hydroxy group, an oxybenzyl group, an —O—R$^{1a}$ group, or an —NH—R$^{1b}$ group, where R$^{1a}$ and R$^{1b}$ each independently represent an unsubstituted or substituted, linear or branched alkyl group having 1 to 12 carbon atoms;
R$^2$ represents a hydrogen atom, an unsubstituted or substituted, linear or branched alkyl group having 1 to 12 carbon atoms, or an unsubstituted or substituted, linear or branched alkylcarbonyl group having 1 to 24 carbon atoms; R$^{3a}$, R$^{3b}$, R$^{4a}$, and R$^{4b}$ each independently represent a methylene group or an ethylene group;
R$^{5a}$ and R$^{5b}$ each independently represent —O— or —NH—;
R$^{6a}$ and R$^{1b}$ each independently represent an unsubstituted or substituted aliphatic hydrocarbon group having 7 to 12 carbon atoms that may contain an alicycle;
R$^{7a}$ and R$^{7b}$ are each independently selected from groups identical to or different from each other in the group consisting of the following groups:

$$—NH—(CH_2)_{p1}—[NH—(CH_2)_{q1}—]_{r1}NH_2 \qquad (i);$$

$$—NH—(CH_2)_{p2}—N[—(CH_2)_{q2}—NH_2]_2 \qquad (ii);$$

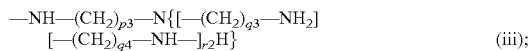

(iii);

and

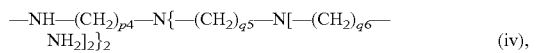

(iv), where p1 to p4, q1 to q6, and r1 and r2 each independently represent an integer of from 1 to 5;

$R^8$ represents a side chain of an amino acid selected from the group consisting of ornithine, lysine, homolysine, arginine, homoarginine, and histidine;

m represents an integer of 9 or more;

n represents an integer of from 0 to m;

x represents an integer of from 2 to 300;

y represents an integer of from 0 to x; and z represents an integer of from 0 to x, provided that a relationship of y+z≤x and a relationship of 11≤m+x≤400 are satisfied, and repeating units in the formula (1) may be randomly present.

In one embodiment, the $R^{6a}$ and $R^{6b}$ each independently represent an unsubstituted or substituted aliphatic hydrocarbon group having 7 to 12 carbon atoms that contains an alicycle.

In one embodiment, in the formula (1), a relationship of (m+x)×0.33≤m≤(m+x)×0.82 is satisfied.

In one embodiment, the $R^{7a}$ and $R^{7b}$ each represent the group (i).

According to another embodiment of the present invention, there is provided an amphiphilic poly(amino acid) for nucleic acid delivery, which is represented by the following formula (1'):

[Chem. 2]

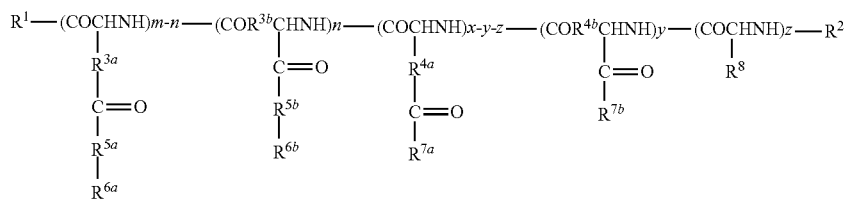

where:

$R^1$ represents a hydroxy group, an oxybenzyl group, an —O—$R^{1a}$ group, or an —NH—$R^{1b}$ group, where $R^{1a}$ and $R^{1b}$ each independently represent an unsubstituted or substituted, linear or branched alkyl group having 1 to 12 carbon atoms;

$R^2$ represents a hydrogen atom, an unsubstituted or substituted, linear or branched alkyl group having 1 to 12 carbon atoms, or an unsubstituted or substituted, linear or branched alkylcarbonyl group having 1 to 24 carbon atoms;

$R^{3a}$, $R^{3b}$, $R^{4a}$, and $R^{4b}$ each independently represent a methylene group or an ethylene group;

$R^{5a}$ and $R^{5b}$ each independently represent —O— or —NH—;

$R^{6a}$ and $R^{6b}$ each independently represent an unsubstituted or substituted aliphatic hydrocarbon group having 7 to 12 carbon atoms that may contain an alicycle;

$R^{7a}$ and $R^{7b}$ are each independently selected from groups identical to or different from each other in the group consisting of the following groups:

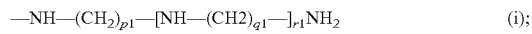

(i);

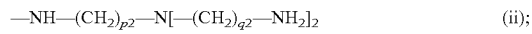

(ii);

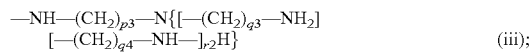

(iii);

and

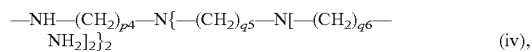

(iv), where p1 to p4, q1 to q6, and r1 and r2 each independently represent an integer of from 1 to 5;

$R^8$ represents a side chain of an amino acid selected from the group consisting of ornithine, lysine, homolysine, arginine, homoarginine, and histidine;

m and x represent integers that satisfy a relationship of (m+x)×0.33≤m≤(m+x)×0.82 and a relationship of 11≤m+x≤400;

n represents an integer of from 0 to m;

y represents an integer of from 0 to x; and z represents an integer of from 0 to x, provided that a relationship of y+z≤x is satisfied, and repeating units in the formula (1') may be randomly present.

In one embodiment, the $R^{6a}$ and $R^{6b}$ each independently represent an unsubstituted or substituted aliphatic hydrocarbon group having 7 to 12 carbon atoms that contains an alicycle.

In one embodiment, the m represents an integer of 5 or more.

In one embodiment, the $R^{7a}$ and $R^{7b}$ each represent the group (i).

According to another aspect of the present invention, there is provided a block copolymer, including:

a poly(amino acid) chain segment derived from the amphiphilic poly(amino acid); and a hydrophilic polymer chain segment.

According to still another aspect of the present invention, there is provided a complex, including:

the amphiphilic poly(amino acid) or the block copolymer; and a nucleic acid.

In one embodiment, the complex further includes a protein.

In one embodiment, the nucleic acid includes at least one kind selected from mRNA, plasmid DNA, donor DNA, sgRNA, CRISPER RNA (crRNA), siRNA, micro RNA, shRNA, an antisense nucleic acid, a decoy nucleic acid, an aptamer, and a ribozyme.

According to still another aspect of the present invention, there is provided a complex, including:
the amphiphilic poly(amino acid) or the block copolymer; and
a protein.

Advantageous Effects of Invention

The amphiphilic poly(amino acid) of the present invention has, in addition to a cationic side chain, a predetermined number or more of hydrophobic side chains each containing a predetermined aliphatic hydrocarbon group. By virtue of having such configuration, the amphiphilic poly(amino acid) of the present invention can suitably introduce nucleic acids including mRNA into cells.

BRIEF DESCRIPTION OF DRAWINGS

FIG. 1 are gel images after electrophoresis of polyplex solutions of various PAsp(R/DET)s and FLuc mRNA.

FIG. 2A is a graph for showing photoluminescence intensities of C2C12 cells transfected with polyplexes each containing GLuc mRNA, and FIG. 2B is a graph for showing photoluminescence intensities of Neuro-2a cells transfected with polyplexes each containing GLuc mRNA (for each polyplex, a right bar represents a result for N/P=5, and a left bar represents a result for N/P=3). All results are expressed as mean±SD (n=4).

FIG. 3-1: FIG. 3-1A is a graph for showing photoluminescence intensities of cultured C2C12 cells transfected with GLuc mRNA in an amount of 50 ng mRNA/well using PAsp(CHE/DET)s having different introduction numbers of CHE moieties, and FIG. 3-1B is a graph for showing photoluminescence intensities of cultured C2C12 cells transfected with GLuc mRNA in an amount of 50 ng mRNA/well using PAsp(CHE/DET)s or PAsp(DET)s having different degrees of polymerization. All results are expressed as mean±SD (n=4).

FIG. 3-2 is a graph for showing a relationship between: ratios (LogP; LogP=Log($S_{OCTANOL}/S_{HEPES}$)) of solubility ($S_{OCTANOL}$) in 1-octanol to solubility ($S_{HEPES}$) in 10 mM HEPES buffer (pH 7.3) of various PAsp(R/DET)s at room temperature; and photoluminescence intensities of C2C12 cells transfected with polyplexes (N/P=5) of the respective PAsp(R/DET)s and GLuc mRNA. All results are expressed as mean±SD (n=4).

FIG. 4: FIG. 4A is a graph for showing a dose-dependent GLuc expression profile of a CHE-polyplex (DP=26, N/P=5), and FIG. 4B is a graph for showing time-dependent GLuc expression profiles of CHE-, OCT-, and DET-polyplexes (DP=26, N/P=5). All results are expressed as mean±SD (n=4).

FIG. 5 is a graph for showing viabilities of C2C12 cells treated with varying concentrations of a CHE-polyplex (DP=26, N/P=5, using GLuc mRNA) for 24 h.

FIG. 6 are graphs for showing uptake profiles of polyplexes with Cy5-GLuc mRNA (DP=26, N/P=5, 500 ng mRNA/well) into cultured C2C12 cells in 4-h incubation. In each of the graphs, cells treated with a buffer are shown as a control (The sharper peak positioned on the left side and having a pale color corresponds to the control).

FIG. 7 is a graph for showing quantitative evaluation results of FLuc mRNA expression levels after intracerebroventricular administration to mice. Results are expressed as mean±SD (n=3).

FIG. 8 is a graph for showing photoluminescence intensities of Neuro-2a cells transfected with polyplexes each containing GLuc mRNA. Results are expressed as mean±SD (n=4).

FIGS. 9A and 9B are confocal laser scanning micrographs of Ai9 mouse-derived hepatocytes transfected with polyplexes containing S. pyogenes Cas9 (SpCas9) mRNA and sgRNA.

FIG. 10 is a diagram for illustrating an in vitro and in vivo evaluation system for genome editing efficiency.

FIGS. 11A and 11B are micrographs of brain slices after intracerebroventricular administration of polyplexes containing SpCas9 mRNA and sgRNA.

FIG. 12 is a graph for showing photoluminescence intensities of Jurkat cells transfected with polyplexes each containing GLuc mRNA. Results are expressed as mean±SD (n=4).

DESCRIPTION OF EMBODIMENTS

A. Amphiphilic Poly(amino Acid)

A-1. First Embodiment

An amphiphilic poly(amino acid) according to a first embodiment of the present invention is represented by the following formula (1). The amphiphilic poly(amino acid) can typically form a complex through an interaction with a nucleic acid, such as mRNA, under a physiological condition (pH 7.4) to be suitably taken up by cells.

[Chem. 3]

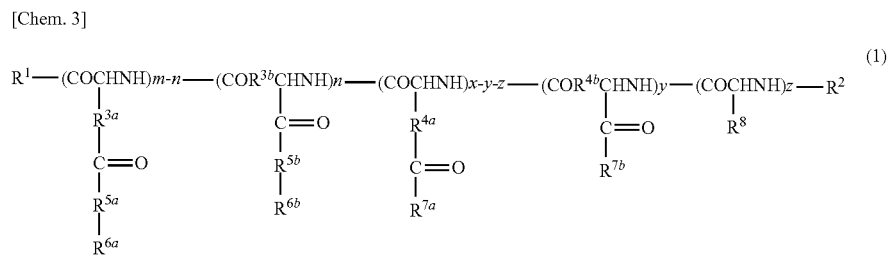

(1)

In the formula:

$R^1$ represents a hydroxy group, an oxybenzyl group, an —O—$R^{1a}$ group, or an —NH—$R^{1b}$ group, where $R^{1a}$ and $R^{1b}$ each independently represent an unsubstituted or substituted, linear or branched alkyl group having 1 to 12 carbon atoms;

$R^2$ represents a hydrogen atom, an unsubstituted or substituted, linear or branched alkyl group having 1 to 12 carbon atoms, or an unsubstituted or substituted, linear or branched alkylcarbonyl group having 1 to 24 carbon atoms;

$R^{3a}$, $R^{3b}$, $R^{4a}$, and $R^{4b}$ each independently represent a methylene group or an ethylene group;

$R^{5a}$ and $R^{5b}$ each independently represent —O— or —NH—;

$R^{6a}$ and $R^{6b}$ each independently represent an unsubstituted or substituted aliphatic hydrocarbon group having 7 to 12 carbon atoms that may contain an alicycle (cycloalkyl ring);

$R^{7a}$ and $R^{7b}$ are each independently selected from groups identical to or different from each other in the group consisting of the following groups:

$$-NH-(CH_2)_{p1}-[NH-(CH2)_{q1}-]_{r1}NH_2 \quad (i);$$

$$-NH-(CH_2)_{p2}-N[-(CH_2)_{q2}-NH_2]_2 \quad (ii);$$

$$-NH-(CH_2)_{p3}-N\{[-(CH_2)_{q3}-NH_2][-(CH_2)_{q4}-NH-]_{r2}H\} \quad (iii);$$

and $$-NH-(CH_2)_{p4}-N\{-(CH_2)_{q5}-N[-(CH_2)_{q6}-NH_2]_2\}_2 \quad (iv),$$

where p1 to p4, q1 to q6, and r1 and r2 each independently represent an integer of from 1 to 5;

$R^8$ represents a side chain of an amino acid selected from the group consisting of ornithine, lysine, homolysine, arginine, homoarginine, and histidine;

m represents an integer of 9 or more;
n represents an integer of from 0 to m;
x represents an integer of from 2 to 300;
y represents an integer of from 0 to x; and
z represents an integer of from 0 to x, provided that a relationship of y+z≤x and a relationship of 11≤m+x≤400 are satisfied, and repeating units in the formula (1) may be randomly present.

In the formula (1), examples of the linear or branched alkyl group having 1 to 12 carbon atoms defined in the groups of $R^{1a}$, $R^{1b}$, and $R^2$ may include a methyl group, an ethyl group, a n-propyl group, an isopropyl group, a n-butyl group, a sec-butyl group, a tert-butyl group, a n-hexyl group, a decyl group, and an undecyl group.

Reference may be made to the examples described above, for a linear or branched alkyl moiety having 1 to 12 carbon atoms in the linear or branched alkylcarbonyl group having 1 to 24 carbon atoms defined in the group of $R^2$. As an alkyl moiety having 13 or more carbon atoms, there may be given, for example, a tridecyl group, a tetradecyl group, a pentadecyl group, a nonadecyl group, a docosanyl group, and a tetracosyl group.

A substituent in the case where the alkyl group or the alkyl moiety is "substituted" is not limited, and examples thereof may include a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkylsiloxy group, a siloxy group, and a silylamino group, or an acetalated formyl group, a formyl group, and a halogen atom, such as a chlorine atom or a fluorine atom. Herein, for example, the expression "$C_{1-6}$" means that the number of carbon atoms is from 1 to 6.

In the formula (1), the respective repeating units are bonded to each other in any appropriate order, and may have a random structure, or may have a block structure. When both of $R^{3a}$ and $R^{3b}$ each represent an ethylene group, a poly(amino acid) in which n=0 or a poly(amino acid) in which m−n=0 is typically represented. The former represents, for example, poly(α-glutamic acid), which is obtained by the polymerization of an N-carboxylic anhydride of glutamic acid γ-benzyl ester, and the latter represents, for example, poly(γ-glutamic acid), which is produced by a bacterial strain of the genus *Bacillus* bacteria, such as *Bacillus natto*. Meanwhile, when both of $R^{3a}$ and $R^{3b}$ each represent a methylene group, it is understood that the respective repeating units having those groups may coexist with each other. The same holds true for $R^{4a}$ and $R^{4b}$.

The group of each of $R^{6a}$ and $R^{6b}$ in the case of containing an alicycle may be represented by the following formula (2). The alicycle means a saturated or unsaturated carbocycle having no aromaticity.

[Chem. 4]

$$-R^{6c}-\underset{}{\underset{}{\bigcirc}}(R^{6d})_{k2} \quad (2)$$

In the formula (2), the group of $R^{6c}$ represents an alkylene group having 1 to 7 carbon atoms, the group of $R^{6d}$ represents an alkyl group having 1 to 3 carbon atoms, the ring A represents a cycloalkyl ring or cycloalkenyl ring having 3 to 9 carbon atoms that may be substituted with k2 $R^{6d}$(s), and k2 represents an integer of from 0 to 2, provided that the number of carbon atoms contained in the group of the formula (2) falls within the range of from 7 to 12, preferably from 7 to 10.

The ring A represents, for example, a cycloalkyl ring or cycloalkenyl ring having 3 to 8 carbon atoms, preferably a cycloalkyl ring or cycloalkenyl ring having 4 to 7 carbon atoms, and specific examples thereof may include a cyclopentyl ring, a cyclopentenyl ring, a cyclohexyl ring, and a cyclohexenyl ring.

The group of $R^{6c}$ may be, for example, an alkylene group having 1 to 5 carbon atoms, and may be preferably an ethylene group, a propylene group, or a butylene group.

The group of $R^{6d}$ is preferably a methyl group or an ethyl group. k2 may represent 0 or 1.

In one embodiment, the group of each of $R^{6a}$ and $R^{6b}$ may be a cyclooctylethyl group, a cycloheptylmethyl group, a cycloheptylethyl group, a cyclohexylmethyl group, a cyclohexylethyl group, a cyclohexylpropyl group, a cyclohexylbutyl group, a cyclopentylethyl group, a cyclopentylpropyl group, a cyclopentylbutyl group, a cyclopentylpentyl group, a cyclobutylpropyl group, a cyclobutylbutyl group, a cyclobutylpentyl group, a cyclopropylbutyl group, a cyclopropylpentyl group, a cyclopropylhexyl group, a 1-cyclohexene-1-ethyl group, a 2-cyclohexene-1-ethyl group, or a 3-cyclohexene-1-ethyl group.

The group of each of $R^{6a}$ and $R^{6b}$ in the case of containing no alicycle may be a linear or branched alkyl group having 7 to 12 carbon atoms, preferably 7 to 10 carbon atoms. Specific examples thereof include a heptyl group, an octyl group, a nonyl group, and a decyl group.

The groups selected from the group consisting of:

$$-NH-(CH_2)_{p1}-[NH-(CH2)_{q1}-]_{r1}NH_2 \quad (i)$$

$$-NH-(CH_2)_{p2}-N[-(CH_2)_{q2}-NH_2]_2 \quad (ii)$$

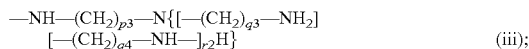

and

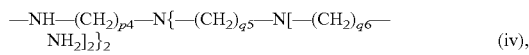

defined in the groups of $R^{7a}$ and $R^{7b}$ are preferably groups identical to each other, and are each more preferably the group of the formula (i). In addition, p1 to p4 and q1 to q6 each independently represent preferably 2 or 3, more preferably 2. Meanwhile, r1 and r2 each independently represent an integer of from 1 to 3.

The groups of $R^{7a}$ or $R^{7b}$ described above have two (or more) varying amino groups, and each of the amino groups show different pKa values. At pH 7.4, which is a physiological condition, the amino groups are in a partially protonated state, and hence the poly(amino acid) of the formula (1) can suitably form a complex (e.g., a polyion complex) through an electrostatic interaction with a nucleic acid. When the complex is taken up into an endosome (pH 5.5), the protonation of the groups of $R^{7a}$ or $R^{7b}$ can further proceed to promote endosomal escape on the basis of a buffering effect (or a proton sponge effect).

The group of $R^8$ described above is preferably a side chain of ornithine, lysine, homolysine, arginine, or homoarginine.

In the formula (1), m represents the number of repetitions of hydrophobic amino acid residues each having introduced therein an aliphatic hydrocarbon group having a predetermined number of carbon atoms, and x represents the number of repetitions of cationic amino acid residues. m represents an integer of 9 or more, preferably 10 or more. x represents an integer of from 2 to 300, preferably an integer of from 5 to 250, more preferably an integer of from 10 to 200. In addition, m+x is an integer of from 11 to 400, preferably an integer of from 20 to 300, more preferably an integer of from 20 to 250. The upper limit of m+x may be 100, 80, 60, or 40.

In one embodiment, x and m satisfy a relationship of preferably (m+x)×0.33≤m≤(m+x)×0.82, more preferably (m+x)×0.35≤m≤(m+x)×0.75, still more preferably (m+x)×0.35≤m≤(m+x)×0.70, still more preferably (m+x)×0.35≤m≤(m+x)×0.65, still more preferably (m+x)×0.38≤m≤(m+x)×0.6. When x and m satisfy such relationship, a nucleic acid, such as mRNA, can be introduced into cells with excellent efficiency.

In one embodiment, the degree of hydrophobicity (LogP) of the amphiphilic poly(amino acid) represented by the formula (1) is preferably −2.4 or higher, more preferably higher than −2.4 and −1.80 or lower. Herein, the degree of hydrophobicity (LogP) refers to the ratio of solubility ($S_{OCTANOL}$) in 1-octanol to solubility ($S_{HEPES}$) in 10 mM HEPES buffer (pH 7.3) of the amphiphilic poly(amino acid) at room temperature (e.g., 25° C.), and may be determined on the basis of the equation: $LogP = Log(S_{OCTANOL}/S_{HEPES})$. Through the use of the amphiphilic poly(amino acid) having such degree of hydrophobicity, a nucleic acid, such as mRNA, can be introduced into cells with high efficiency. The degree of hydrophobicity (LogP) may be determined by, for example, a method described in Examples.

A-2. Second Embodiment

An amphiphilic poly(amino acid) according to a second embodiment of the present invention is represented by the following formula (1'). The amphiphilic poly(amino acid) can typically form a complex through an interaction with a nucleic acid, such as mRNA, under a physiological condition (pH 7.4) to be suitably taken up by cells.

[Chem. 5]

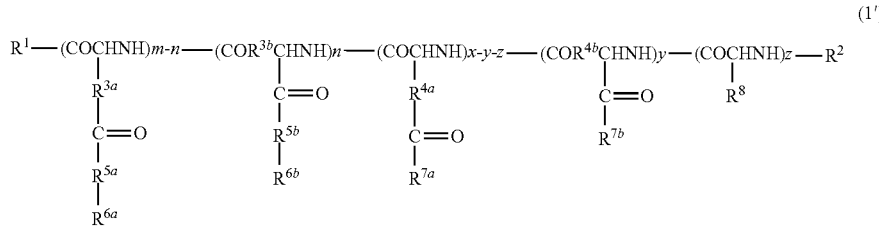

In the formula:
$R^1$ represents a hydroxy group, an oxybenzyl group, an —O—$R^{1a}$ group, or an —NH—$R^{1b}$ group, where $R^{1a}$ and $R^{1b}$ each independently represent an unsubstituted or substituted, linear or branched alkyl group having 1 to 12 carbon atoms;

$R^2$ represents a hydrogen atom, an unsubstituted or substituted, linear or branched alkyl group having 1 to 12 carbon atoms, or an unsubstituted or substituted, linear or branched alkylcarbonyl group having 1 to 24 carbon atoms;

$R^{3a}$, $R^{3b}$, $R^{4a}$, and $R^{4b}$ each independently represent a methylene group or an ethylene group;

$R^{5a}$ and $R^{5b}$ each independently represent —O— or —NH—;

$R^{6a}$ and $R^{6b}$ each independently represent an unsubstituted or substituted aliphatic hydrocarbon group having 7 to 12 carbon atoms that may contain an alicycle;

$R^{7a}$ and $R^{7b}$ are each independently selected from groups identical to or different from each other in the group consisting of the following groups:

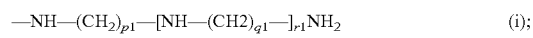

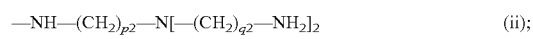

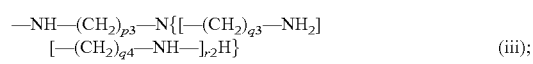

and

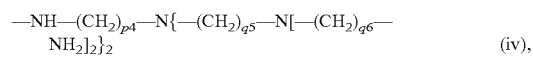

where p1 to p4, q1 to q6, and r1 and r2 each independently represent an integer of from 1 to 5;

$R^8$ represents a side chain of an amino acid selected from the group consisting of ornithine, lysine, homolysine, arginine, homoarginine, and histidine;

m and x represent integers that satisfy a relationship of $(m+x) \times 0.33 \le m \le (m+x) \times 0.82$ and a relationship of $11 \le m+x \le 400$;

n represents an integer of from 0 to m;

y represents an integer of from 0 to x; and z represents an integer of from 0 to x, provided that a relationship of $y+z \le x$ is satisfied, and repeating units in the formula (1') may be randomly present.

The same descriptions as those of the groups of $R^1$ to $R^8$ in the formula (1) apply to the groups of $R^1$ to $R^8$ in the formula (1'), respectively, and preferred groups are also the same.

In the formula (1'), m represents the number of repetitions of hydrophobic amino acid residues each having introduced therein an aliphatic hydrocarbon group having a predetermined number of carbon atoms, and x represents the number of repetitions of cationic amino acid residues. Preferably, m represents an integer of 5 or more, and may represent an integer of, for example, 6 or more, 7 or more, or 8 or more. In addition, x represents typically an integer of from 2 to 250, preferably an integer of from 5 to 250, more preferably an integer of from 10 to 200. In addition, m+x is an integer of from 11 to 400, preferably an integer of from 15 to 300, more preferably an integer of from 20 to 300, still more preferably an integer of from 20 to 250. The upper limit of m+x may be 100, 80, 60, or 40.

In the formula (1'), x and m satisfy a relationship of $(m+x) \times 0.33 \le m \le (m+x) \times 0.82$, preferably $(m+x) \times 0.35 \le m \le (m+x) \times 0.75$, more preferably $(m+x) \times 0.35 \le m \le (m+x) \times 0.70$, still more preferably $(m+x) \times 0.35 \le m \le (m+x) \times 0.65$, still more preferably $(m+x) \times 0.38 \le m \le (m+x) \times 0.6$. When x and m satisfy such relationship, a nucleic acid, such as mRNA, can be introduced into cells with excellent efficiency.

In one embodiment, the degree of hydrophobicity (LogP) of the amphiphilic poly(amino acid) represented by the formula (1') is preferably −2.4 or higher, more preferably higher than −2.4 and −1.80 or lower. Herein, the degree of hydrophobicity (LogP) refers to the ratio of solubility ($S_{OCTANOL}$) in 1-octanol to solubility ($S_{HEPES}$) in 10 mM HEPES buffer (pH 7.3) of the amphiphilic poly(amino acid) at room temperature (e.g., 25° C.), and may be determined on the basis of the equation: $LogP=Log(S_{OCTANOL}/S_{HEPES})$. Through the use of the amphiphilic poly(amino acid) having such degree of hydrophobicity, a nucleic acid, such as mRNA, can be introduced into cells with high efficiency.

The amphiphilic poly(amino acid) represented by the formula (1) or the formula (1') may be produced by, for example, polymerizing N-carboxylic anhydrides (NCA) of protected amino acids known per se, such as β-benzyl-L-aspartate, γ-benzyl-L-glutamate, and Nε-Z-L-lysine, to produce a poly(amino acid) ester, and then performing aminolysis using amines corresponding to the groups of $R^{6a}$, $R^{6b}$, $R^{7a}$, $R^{7b}$, and $R^8$. The groups of $R^{6a}$, $R^{6b}$, $R^{7a}$, $R^{7b}$, and $R^8$ may be introduced at desired introduction ratios by changing the ratios of the respective amines to be used at the time of the aminolysis.

A structural change due to nucleophilic attack by an amine (such as the formation of an imide ring through the dealcoholization of an amino acid ester residue) may occur in some amino acid ester residues during the process of the synthesis, and a poly(amino acid) further containing a residue which has undergone such structural change is herein also regarded as included in the formula (1) or the formula (1'). In this case, the residue which has undergone the structural change is not included in the amino acid residue. In addition, some NH groups and $NH_2$ groups in the cationic amino acid residues may be converted to salts (mainly hydrochlorides) owing to the use of an acid (mainly hydrochloric acid) in the synthesis process, and an amphiphilic poly(amino acid) containing such structure is herein also regarded as included in the formula (1) or the formula (1'). That is, some NH groups and $NH_2$ groups in the groups of $R^{7a}$, $R^{7b}$, and $R^8$ may be converted to salts (such as hydrochlorides).

B. Block Copolymer

According to another aspect of the present invention, there is provided a block copolymer. The block copolymer has a structure in which the amphiphilic poly(amino acid) represented by the formula (1) or the formula (1') described in the section A and a hydrophilic polymer are bonded to each other via a linking group as required, and includes a poly(amino acid) chain segment derived from the amphiphilic poly(amino acid) and a hydrophilic polymer chain segment. By virtue of having such structure, the block copolymer of the present invention can form a polymer particle (e.g., a polymer micelle) showing satisfactory retentivity in circulating blood while keeping the characteristics of the amphiphilic poly(amino acid) itself.

In one embodiment, the block copolymer is represented by the formula: A-L-B (where A represents a hydrophilic polymer chain segment, B represents a poly(amino acid) segment derived from the amphiphilic poly(amino acid) described in the section A, and L represents a direct bond or a linking group). In the formula, the hydrophilic polymer chain segment represented by A may be a single chain, or may be branched into two or more chains.

Any appropriate hydrophilic polymer may be adopted as the hydrophilic polymer. Examples of the hydrophilic polymer include poly(ethylene glycol), a poly(saccharide), poly (vinylpyrrolidone), poly(vinyl alcohol), poly(acrylamide), poly(acrylic acid), poly(methacrylamide), poly(methacrylic acid), poly(methacrylic acid ester), poly(acrylic acid ester), a poly(amino acid), poly(malic acid), and derivatives thereof. Specific examples of the poly(saccharide) include starch, dextran, fructan, and galactan. Of those, poly(ethylene glycol) may be preferably used because end-reactive poly(ethylene glycol)s having various functional groups at ends thereof are commercially available and poly(ethylene glycol)s having various molecular weights are commercially available and easily available.

The poly(ethylene glycol) may have a molecular weight (Da) of, for example, from 800 to 80,000, preferably from 2,000 to 60,000, more preferably from 5,000 to 40,000.

The block copolymer of the present invention may be preferably represented by the following formula (3) or (4).

[Chem. 6]

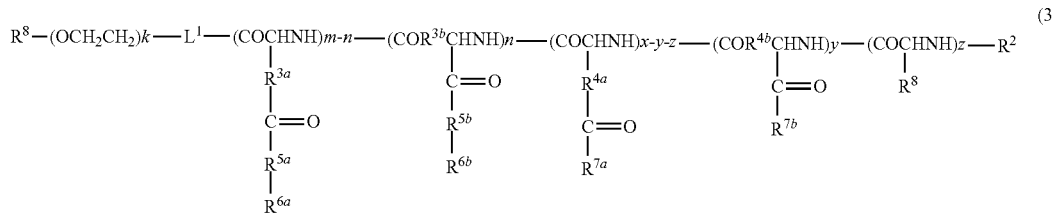

(3)

[Chem. 7]

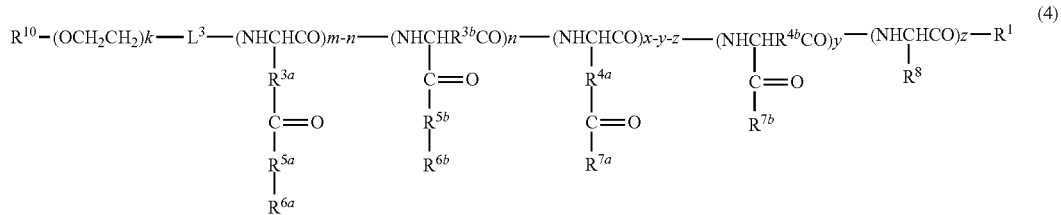

(4)

In each of the formulae:
$R^1$ to $R^8$, m, n, x, y, and z have the same meanings as defined for the formula (1) or the formula (1');
$L^1$ and $L^3$ each represent a linking group;
$R^9$ and $R^{10}$ each independently represent a hydrogen atom or an unsubstituted or substituted, linear or branched alkyl group having 1 to 12 carbon atoms; and
k represents an integer of from 20 to 20,000.

$L^1$ and $L^3$ each represent a linking moiety between the hydrophilic polymer chain segment and the amphiphilic poly(amino acid) segment, and may each represent any appropriate linking group. The linking group represented by $L^1$ may be, for example, a linking group selected from —NH—, —O—, —O—$L^2$—NH—, —CO—, —CH$_2$—, and —O—$L^2$—S—$L^2$—NH— (where $L^2$s each independently represent an alkylene group having 1 to 6 carbon atoms). $L^3$ may represent, for example, a linking group selected from —OCO—$L^4$—CO— and —NHCO—$L^4$—CO— (where $L^4$ represents an alkylene group having 1 to 6 carbon atoms).

Examples of the linear or branched alkyl group having 1 to 12 carbon atoms defined in the groups of $R^9$ and $R^{10}$ may include a methyl group, an ethyl group, a n-propyl group, an isopropyl group, a n-butyl group, a sec-butyl group, a tert-butyl group, a n-hexyl group, a decyl group, and an undecyl group. In addition, a substituent in the "substituted" case may be similar to the substituent exemplified for the groups of $R^1$ and $R^2$ in the formula (1). Alternatively, the groups of $R^9$ and $R^{10}$ may each be substituted with a group containing a target binding site. When the target binding site is introduced into an end of the hydrophilic polymer chain segment, a delivery property to a desired target site can be enhanced.

The group containing a target binding site may be any appropriate group as long as the group has directivity or functionality for a tissue serving as a target, and examples thereof may include groups derived from physiologically active substances, such as an antibody or a fragment thereof, or a protein having any other functionality or target directivity, a peptide, an aptamer, a sugar, such as lactose, and folic acid, and derivatives thereof.

Character "k", which represents the number of repetitions of ethylene glycol (or oxyethylene), represents an integer of from 20 to 20,000, preferably from 40 to 2,000, more preferably from 45 to 1,000.

The block copolymer of the present invention may be formed by, for example, coupling, by a known method, the amphiphilic poly(amino acid) and the hydrophilic polymer, each of which has not been subjected to any treatment or has been purified so as to achieve a narrow molecular weight distribution as required. In addition, for example, the block copolymer of the general formula (3) may be produced by: carrying out anionic living polymerization using an initiator capable of providing $R^9$ to form a poly(ethylene glycol) chain; then introducing an amino group at the side of the growing end; polymerizing N-carboxylic anhydrides (NCA) of protected amino acids, such as β-benzyl-L-aspartate, γ-benzyl-L-glutamate, and Nε-Z-L-lysine, from the amino end; and introducing the groups of $R^{6a}$, $R^{6b}$, $R^{7a}$, $R^{7b}$, and $R^8$ into side chains of the resultant poly(amino acid) segment through aminolysis or transesterification.

C. Complex with nucleic acid

According to still another aspect of the present invention, there is provided a complex (hereinafter sometimes referred to as polyplex) including the amphiphilic poly(amino acid) described in the section A or the block copolymer described in the section B and a nucleic acid. Each of the amphiphilic poly(amino acid) and the block copolymer has positive charge derived from cationic groups, and hence can form a complex with the nucleic acid having negative charge through electrostatic interaction.

The nucleic acid means a poly- or oligonucleotide using nucleotides, each of which is formed of a purine or pyrimidine base, a pentose, and phosphoric acid, as basic units, and examples thereof may include oligo- or poly-double-stranded RNA, oligo- or poly-double-stranded DNA, oligo- or poly-single-stranded DNA, and oligo- or poly-single-stranded RNA. In addition, the examples also include an oligo- or poly-double-stranded nucleic acid and an oligo- or poly-single-stranded nucleic acid each containing RNA and DNA in a single strand. Each of the nucleotides contained in the nucleic acid may be a naturally occurring nucleotide or a chemically-modified, non-naturally occurring nucleotide, and may have added thereto an amino group, a thiol group, or a molecule of a fluorescent compound or the like.

The strand length of the nucleic acid (in the case of a double-stranded nucleic acid, the strand length of a portion forming double strands) is not particularly limited, and the nucleic acid may have a relatively short strand of less than 100 bases, for example, from 10 bases to 80 bases, preferably from about 15 bases to about 50 bases, or the nucleic acid may have a relatively long strand of 100 bases or more, preferably from 100 bases to 20,000 bases, more preferably from about 200 bases to about 10,000 bases.

In consideration of the function or action of the nucleic acid, preferred examples of the nucleic acid may include plasmid DNA, donor DNA, mRNA, sgRNA, crRNA, siRNA, micro RNA, shRNA, an antisense nucleic acid, a decoy nucleic acid, an aptamer, and a ribozyme. The nucleic acids may be used alone or in combination thereof.

The particle diameter of the complex may be, for example, from 10 nm to 500 nm, preferably from 20 nm to 300 nm.

The complex may be prepared by mixing the amphiphilic poly(amino acid) or the block copolymer and the nucleic acid at a desired N/P ratio in an aqueous solution buffered as required. From the viewpoint of enhancing the stability and cellular uptake property of the complex under a physiological condition, the N/P ratio is preferably 2 or higher, more preferably 3 or higher, still more preferably 5 or higher. The upper limit of the N/P ratio may be set to, for example, 200 or less. The N/P ratio means a ratio between the molar concentration (N) of protonatable amino groups derived from the side chain of the amphiphilic poly(amino acid) or the block copolymer and the molar concentration (P) of phosphate groups derived from the nucleic acid in the mixed solution.

The complex may further include a protein in addition to the nucleic acid. The protein may be, for example, an RNA-binding protein, which may be included in the complex in the form of a complex with RNA (ribonucleoprotein, RNP). An example of such ribonucleoprotein is a complex of RNA and an RNA-dependent DNA nuclease (specific examples thereof include a complex of sgRNA and Cas9 and a complex of crRNA and Cpf1). Through the use of such complex, a protein having desired activity can be directly introduced into cells to exhibit its action.

An example of the complex including the protein is a complex (GNP/donor DNA/Cas9 RNP/(silica)/amphiphilic poly(amino acid), from inside toward outside of particle) obtained by: adsorbing single-stranded DNA (DNA-SH) having an end SH group and having a sequence complementary to that of donor DNA onto the surface of a gold nanoparticle (GNP); allowing the donor DNA to hybridize with the DNA-SH to form a GNP-donor complex; adsorbing a complex (Cas9 RNP) of sgRNA and Cas9 onto the surface of the GNP-donor complex; coating the resultant with silica as required; and then electrostatically bonding the resultant and the amphiphilic poly(amino acid) to each other. The details of the complex are disclosed in Nature Biomedical Engineering, volume 1, pages 889-901 (2017), in which the complex is shown to be effective for genome editing.

D. Complex with Anionic Compound Other than Nucleic Acid

The amphiphilic poly(amino acid) described in the section A or the block copolymer described in the section B can also form a complex with an anionic compound other than the nucleic acid, which has more negative charges than positive charges in an aqueous medium with a physiological pH (e.g., pH7.4), through electrostatic interaction, and introduce the anionic compound into the cell. The example of the anionic compound includes a protein, a poly(saccharide), and a lipid. In one embodiment, there is provided a complex including the amphiphilic poly(amino acid) described in the section A or the block copolymer described in the section B and the protein. The example of the protein includes an anionic protein having physiological activity such as an antibody, a ligand, a hormone, and an enzyme. In this context, the anionic protein may be a protein whose charge is artificially converted so as to have more negative charges than positive charges in an aqueous medium with a physiological pH. Such charge-converted protein and the complex of the amphiphilic poly(amino acid) described in the section A or the block copolymer described in the section B and the protein can be prepared, for example, by using a method similar to the method described in the section C or a method described in Angew. Chem. Int. Ed., 2009, 48, 5309-5312.

EXAMPLES

Now, the present invention is specifically described by way of Examples. However, the present invention is by no means limited to these Examples.

Test Example A

1. Synthesis of Poly(β-benzyl-L-aspartate)s (PBLAs)

Poly(β-benzyl-L-aspartate)s (PBLAs) having degrees of polymerization of 26, 63 and 121 were prepared in accordance with a method described in J. Am. Chem. Soc. 2008, 130, 16287. The degrees of polymerization of β-benzyl-L-aspartate were each calculated from the peak intensity ratio of phenyl protons to methyl protons ($CH_3(CH_2)_3NH$, $\delta$=0.8) in $^1H$ NMR (400 MHz, JNM-ECS 400 (manufactured by JEOL)). In addition, for the PBLAs having degrees of polymerization of 26, 63, and 121, polydispersities ($M_w/M_n$) were determined by gel permeation chromatography, and found to be 1.18, 1.19, and 1.34, respectively.

2. Synthesis of Amphiphilic Polyaspartamide Derivatives (PAsp(R/DET)s)

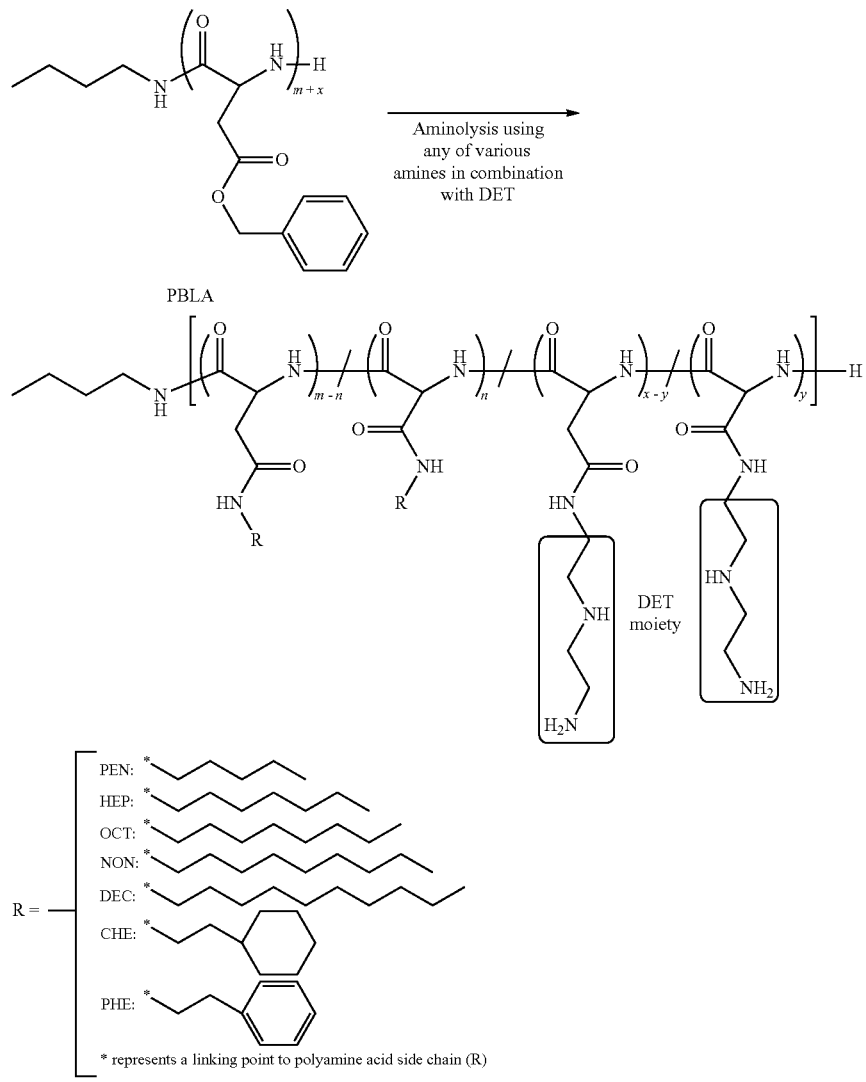

As shown in the synthetic route above, various PAsp(R/DET)s serving as amphiphilic poly(amino acid)s were prepared by the simultaneous aminolysis reaction of PBLA with various amines and diethylenetriamine (DET). In the resultant poly(amino acid)s, u-aspartic acid residues and β-aspartic acid residues are randomly present, and their side chains have DET moieties or groups represented by R introduced at various ratios.

As a specific example, a synthesis method in the case where R represents a cyclohexylethyl group is described below. PBLA (DP=26, 30 mg) was dissolved in NMP (2 mL) and cooled to 4° C. The resultant PBLA solution was added dropwise to the mixture of DET (790 μL) and 2-cyclohexylethylamine (2.14 mL) (molar ratio=1:2), and the solution was stirred for 1 h at 4° C. under argon atmosphere. The reaction liquid was added dropwise to cold 5 M HCl (5 mL) for neutralization. The polymer product was purified by dialysis against 0.01 M HCl at 4° C. and then distilled water at 4° C. The dialyzed solution was lyophilized to obtain a solid powder. The obtained powder was dissolved in methanol (4 mL) with a small amount of triethylamine and then precipitated into an excess amount of diethyl ether to completely remove unreacted 2-cyclohexylethylamine. The precipitate was filtered and dissolved in distilled water. The polymer was further purified by dialysis against 0.01 M HCl at 4° C. and then distilled water at 4° C. The dialyzed solution was lyophilized to obtain the final product. Quantitative conversion of benzyl ester groups to DET moieties and cyclohexylethyl (CHE) moieties in side chains was confirmed in the $^1$H NMR spectrum (10 mg/mL, 80° C.).

The other PAsp(R/DET)s or PAsp(DET)s were also synthesized according to the similar procedures. The introduction ratios of DET moieties and R moieties were adjusted by changing the mixing ratios of DET and each amine to be allowed to react with PBLA.

The resultant poly(amino acid)s are shown in Table 1.

TABLE 1

| Poly (amino acid) | Degree of polymerization (DP) | R | Introduction number[*1] | |
|---|---|---|---|---|
| | | | R | DET |
| PAsp (PEN13/DET13) | 26 | Pentyl group | 13 | 13 |
| PAsp (HEP11/DET15) | 26 | Heptyl group | 11 | 15 |
| PAsp (OCT10/DET16) | 26 | Octyl group | 10 | 16 |
| PAsp (NON10/DET16) | 26 | Nonyl group | 10 | 16 |
| PAsp (DEC9/DET17) | 26 | Decyl group | 9 | 17 |
| PAsp (CHE2/DET24) | 26 | 2-Cyclohexylethyl group | 2 | 24 |
| PAsp (CHE8/DET18) | 26 | 2-Cyclohexylethyl group | 8 | 18 |
| PAsp (CHE11/DET15) | 26 | 2-Cyclohexylethyl group | 11 | 15 |
| PAsp (PHE11/DET15) | 26 | Phenyletnyl group | 11 | 15 |
| PAsp (DET26) | 26 | — | 0 | 26 |
| PAsp (CHE32/DET31) | 63 | 2-Cyclohexylethyl group | 32 | 31 |
| PAsp (DET63) | 63 | — | 0 | 63 |
| PAsp (CHE47/DET74) | 121 | 2-Cyclohexylethyl group | 47 | 74 |
| PAsp (DET121) | 121 | — | 0 | 121 |

[*1]Determined by $^1$H NMR

3. Preparation and Characterization of Polyplexes of PAsp(R/DET)s and mRNA (1) Preparation of Polyplexes PAsp(R/DET)s were dissolved in 10 mM HEPES buffer (pH 7.3) and then mixed with mRNA solution (100 ng/L mRNA in 10 mM HEPES buffer, pH 7.3) at N/P ratios of 0, 1, 2, 3, 4, or 5 to prepare polyplex solutions (20 ng/L mRNA). As the mRNA, Firefly luciferase (FLuc) mRNA or Gaussia luciferase (GLuc) mRNA was used. The base sequences of FLuc mRNA and GLuc mRNA are known as GenBank M15077.1 and GenBank AY015993.1, respectively.

(2) Gel Shift Assay

The polyplex solutions prepared using PAsp(R/DET)s with DP=26 and FLuc mRNA were electrophoresed on an agarose gel. The results are shown in FIG. 1.

As shown in FIGS. 1, bands have appeared in high molecular weight regions, confirming the formation of polyplexes. In addition, in the cases of N/P ratios of 2 or higher, bands derived from FLuc mRNA alone disappeared, revealing that all FLuc mRNA molecules formed complexes with the PAsp(R/DET)s at N/P ratios of 2 or higher.

(3) Characterization of Polyplexes

For the polyplexes prepared at N/P ratio=3 and 5 using GLuc mRNA, size (cumulant diameter) and size distribution (polydispersity index (PDI)) were determined by a dynamic light scattering method using a Zetasizer (manufactured by Malvern Instruments) equipped with a He-Ne Laser ($\lambda$=633 nm) at a temperature of 25° C. and a detection angle of 173°. In addition, polyplex zeta potential was measured by an electrophoretic light scattering method using the same apparatus. The results are shown in Table 2.

TABLE 2

| Polypex | Polymer Name | DP | N/P = 3 | | | N/P = 5 | | |
|---|---|---|---|---|---|---|---|---|
| | | | Size (nm) | PDI | Zeta potential (mV) | Size (nm) | PDI | Zeta potential (mV) |
| DET-polypex | PAsp (DET26) | 26 | 129 ± 8 | 0.16 ± 0.04 | 6.8 ± 5.4 | 105 ± 2 | 0.27 ± 0.02 | 23.1 ± 6.1 |
| PEN-polypex | PAsp (PEN13/DET13) | 26 | 129 ± 3 | 0.11 ± 0.03 | 8.1 ± 4.3 | 96 ± 3 | 0.19 ± 0.01 | 19.4 ± 7.3 |
| HEP-polypex | PAsp (HEP11/DET15) | 26 | 109 ± 4 | 0.21 ± 0.02 | 9.7 ± 4.3 | 102 ± 6 | 0.24 ± 0.06 | 23.5 ± 7.0 |
| OCT-polypex | PAsp (OCT10/DET16) | 26 | 157 ± 32 | 0.31 ± 0.11 | 12.7 ± 4.1 | 113 ± 10 | 0.23 ± 0.03 | 21.3 ± 4.9 |
| NON-polypex | PAsp (NON10/DET16) | 26 | 156 ± 11 | 0.25 ± 0.04 | 12.0 ± 5.0 | 117 ± 13 | 0.22 ± 0.02 | 21.8 ± 5.8 |
| DEC-polypex | PAsp (DEC9/DET17) | 26 | 138 ± 7 | 0.31 ± 0.02 | 17.0 ± 4.3 | 131 ± 37 | 0.29 ± 0.07 | 19.8 ± 5.6 |
| CHE-polypex | PAsp (CHE11/DET15) | 26 | 119 ± 17 | 0.21 ± 0.03 | 9.7 ± 6.1 | 103 ± 16 | 0.20 ± 0.04 | 24.4 ± 3.8 |
| PHE-polypex | PAsp (PHE11/DET15) | 26 | 153 ± 15 | 0.11 ± 0.03 | 6.9 ± 4.0 | 102 ± 3 | 0.16 ± 0.03 | 10.2 ± 12.0 |
| CHE(2)-polypex | PAsp (CHE2/DET24) | 26 | 158 ± 3 | 0.03 ± 0.01 | 6.8 ± 5.6 | 101 ± 5 | 0.15 ± 0.04 | 10.6 ± 7.6 |
| CHE(8)-polypex | PAsp (CHE8/DET18) | 26 | 115 ± 1 | 0.10 ± 0.03 | 10.9 ± 7.9 | 108 ± 1 | 0.21 ± 0.01 | 21.0 ± 5.5 |
| CHE(32)-polypex | PAsp (CHE32/DET31) | 63 | 130 ± 5 | 0.21 ± 0.03 | 18.6 ± 4.0 | 98 ± 2 | 0.18 ± 0.02 | 27.9 ± 5.9 |
| CHE(47)-polypex | PAsp (CHE47/DET74) | 121 | 112 ± 4 | 0.18 ± 0.04 | 20.8 ± 5.5 | 92 ± 4 | 0.14 ± 0.01 | 31.3 ± 9.0 |
| DET(63)-polypex | PAsp (DET63) | 63 | 89 ± 9 | 0.19 ± 0.04 | 29.7 ± 8.6 | 76 ± 3 | 0.18 ± 0.01 | 24.2 ± 12.1 |
| DET(121)-polypex | PAsp (DET121) | 121 | 95 ± 3 | 0.17 ± 0.02 | 34.5 ± 8.6 | 79 ± 1 | 0.18 ± 0.02 | 27.9 ± 9.2 |

4. Transfection of Polyplexes in Cultured Cells (1) Evaluation of Protein Expression Efficiency C2C12 cells or Neuro-2a cells were seeded into a 96-well plate at a density of 8,000 cells/well in DMEM containing 10% FBS (DMEM/FBS). On the next day, the medium was replaced with fresh DMEM/FBS. Polyplex solutions (N/P ratio=3 or 5) prepared using GLuc mRNA and various PAsp(R/DET)s were then added to each well at a dose of 50 ng mRNA/well and incubated for 24 h. In a dose-dependent GLuc expression profile test to be described later, the polyplexes were added to each well in an amount of 0.5 ng to 50 ng mRNA/well and incubated for 24 h.

The expression levels of GLuc were determined from the photoluminescence intensity of cell culture medium supernatants using the Luciferase Assay System (manufactured by Promega) for GLuc. The photoluminescence intensities were measured with a luminescence microplate reader (manufactured by Berthold Technologies, "Mithras LB 940"). The results of polyplexes using various PAsp(R/DET)s with DP=26 are shown in FIG. 2A and FIG. 2B. In addition, the results of polyplexes using PAsp(R/DET)s having different introduction numbers of R moieties and the results of polyplexes using PAsp(R/DET)s having different degrees of polymerization are shown in FIG. 3-1A and FIG. 3-1B, respectively. Further, a dose-dependent GLuc expression profile and time-dependent GLuc expression profiles are shown in FIG. 4A and FIG. 4B, respectively. In addition, a relationship between the degrees of hydrophobicity of various PAsp(R/DET)s with DP=26 (specifically, ratios (LogP; LogP=Log($S_{OCTANOL}/S_{HEPES}$)) of solubility ($S_{OCTANOL}$) in 1-octanol to solubility ($S_{HEPES}$) in 10 mM HEPES buffer (pH 7.3) of the respective PAsp(R/DET)s at room temperature) and the photoluminescence intensities of C2C12 cells transfected with polyplexes (N/P=5) of the respective PAsp(R/DET)s and GLuc mRNA are shown in FIG. 3-2. The degrees of hydrophobicity (LogP) were each measured at room temperature in accordance with the following method. The PAsp(R/DET) was dissolved in methanol with a small amount of triethylamine, and Alexa Fluor™647 (Alexa647)—NHS ester (ThermoFisher Scientific) was added, followed by a reaction therebetween. The Alexa647-labeled PAsp(R/DET) (100 μM, 50 μL) was dissolved in 10 mM HEPES buffer (pH 7.3), the solution was mixed with 1-octanol (50 μL), and the mixture was vigorously stirred for 30 min (2,900 rpm, Eppendorf MixMate). The two-phase mixture was briefly centrifuged, and placed at 4° C. for 1 h. The 1-octanol phase was carefully collected, and further placed at 4° C. for 1 h. The remaining 10 mM HEPES buffer (pH 7.3) was centrifuged at 3,300 g for 5 min, and placed at 4° C. for 1 h. The fluorescence intensities of Alexa647 in 1-octanol and 10 mM HEPES buffer (pH 7.3) were measured with a spectrofluorometer (FP-8300, Jasco), and the degree of hydrophobicity (LogP) was calculated by taking the common logarithm of a quotient obtained by dividing the fluorescence intensity derived from the 1-octanol phase by the fluorescence intensity derived from the 10 mM HEPES buffer (pH 7.3) phase.

As shown in FIG. 2A and FIG. 2B, in both the C2C12 cells and the Neuro-2a cells, the polyplexes of Examples (HEP-, OCT-, NON-, DEC-, and CHE-polyplexes) each showed a photoluminescence intensity of more than 100,000. This reveals that GLuc mRNA was efficiently expressed in the cells through the use of each of those polyplexes. Of those, the CHE-polyplex showed a remarkably high photoluminescence intensity of more than 10,000,000. Meanwhile, the PEN-, PHE-, and DET-polyplexes only showed photoluminescence intensities that were about 2 digits to about 6 digits smaller as compared to the corresponding polyplexes of Examples.

As shown in FIG. 3-1A and FIG. 3-1B, with regard to the polyplexes (DP=26) having different introduction numbers of R moieties, the photoluminescence intensities of the polyplexes having introduction numbers of CHE moieties of 2 and 8 were about 5 digits smaller as compared to the polyplexes each having an introduction number of 11. Meanwhile, with regard to the polyplexes having different degrees of polymerization, the polyplexes using PAsp (DET)s tended to have higher photoluminescence intensities as the degree of polymerization increased, but the polyplexes using PAsp(CHE/DET)s showed remarkably high photoluminescence intensities irrespective of the difference in degree of polymerization. In addition, a graph shown in FIG. 3-2 reveals that PAsp(R/DET) having a LogP (Log ($S_{OCTANOL}/S_{HEPES}$)) of −2.4 or higher functions extremely effectively as a carrier in the delivery of a nucleic acid, such as mRNA, into cells.

A dose-dependent GLuc expression profile of a CHE-polyplex (DP=26, N/P=5) was tested in C2C12 cultured cells. As shown in FIG. 4A, the CHE-polyplex showed a dose-dependent increase in photoluminescence intensity at doses of from 0.5 ng to 10 ng mRNA/well, and the increase reached a plateau at the dose of 10 ng mRNA/well.

Time-dependent GLuc expression profiles of CHE-, OCT-, and DET-polyplexes (DP=26, N/P=5) were also measured every 2 h in C2C12 cultured cells. As shown in FIG. 4B, the DET-polyplex showed a low photoluminescence intensity at the background level (500 or less) at all measurement time points. Meanwhile, the photoluminescence intensities of the CHE- and OCT-polyplexes increased with time, and reached extremely high photoluminescence intensities of about 60,000,000 for the former and about 9,000,000 for the latter after 12 h.

(2) Cytotoxicity Evaluation

Cell viability in the presence of a polyplex was measured using a Cell Counting Kit-8 (manufactured by Dojindo). Specifically, C2C12 cells were seeded into a 96-well plate at a density of 8,000 cells/well in DMEM/FBS. On the next day, a CHE-polyplex (N/P=5) was added to the well at varying GLuc mRNA doses and the cells were incubated for 24 h. The medium was replaced with a fresh medium (100 μL) containing the Kit solution (10 μL) and the cells were further incubated for 1 h. After that, the absorbance of the medium was measured at 450 nm. The results are shown in FIG. 5.

As shown in FIG. 5, no reduction in cell viability was found at any of the addition amounts. This suggests that the CHE-polyplex does not have cytotoxicity in those addition amounts.

5. Cellular Uptake Evaluation

C2C12 cells were seeded into a 12-well plate at a density of 100,000 cells/well in DMEM/FBS. On the next day, the medium was replaced with fresh DMEM/FBS, and a polyplex solution (DP=26, N/P=5) using Cy5-labeled GLuc mRNA (Cy5-mRNA) or Cy5-mRNA alone was added to each well at a dose of 500 ng mRNA/well. After 4-h incubation, the medium was removed and the cells were washed with 1 mL of PBS. The cells were treated with a trypsin-EDTA solution for 1 min and suspended in PBS. The cellular uptake of Cy5-mRNA was measured using a flow cytometer ("BD™ LSR II" manufactured by BD Biosciences). The results are shown in FIG. 6.

As shown in FIGS. 6, HEP-, OCT-, NON-, DEC-, and CHE-polyplexes showed remarkably higher cellular uptake of Cy5-mRNA than DET-, PEN-, and PHE-polyplexes.

6. In Vivo mRNA Delivery

The 6 to 8-week-old female BALB/c mice (Charles River Laboratories Japan, Inc.) were anesthetized by inhalation of isoflurane, and were held in the prone position on a stereotaxic instrument (manufactured by Narishige Group). The scalp was sagittally incised in the lengths of from 1.0 cm to 1.5 cm and the calvarium was exposed by blunt dissection. A small hole was perpendicularly created on the sagittal suture of the parietal bone at the 0.5 mm posterior to the bregma by a 1.1 mm diameter trephine bur. A CHE- or DET-polyplex solution (10 µL) containing 4.5 µg FLuc mRNA was administered to the $3^{rd}$ ventricle at the depth of 3.0 mm perpendicular to the brain surface with a Hamilton syringe (using a 30 G syringe) connected to a stereotaxic micromanipulator at a rate of about 2.0 µL/min. Then, the incision was closed using sutures. FLuc mRNA alone and a complex of LIPOFECTAMINE™ 2000 and FLuc mRNA were used as controls. The photoluminescence intensity from the brain was measured 4 h and 24 h after the administration with an IVIS instrument (manufactured by PerkinElmer) equipped with a Living Image Software (manufactured by PerkinElmer), and thus the protein expression efficiency of FLuc mRNA was quantitatively evaluated. The results are shown in FIG. 7.

As shown in FIG. 7, the CHE-polyplexes (DP=26, N/P=3 and 5) showed remarkably high photoluminescence intensities at the time point of 4 h as compared to the DET-polyplex (DP=26, N/P=5) and LIPOFECTAMINE™ 2000. In addition, the CHE-polyplexes showed rapid reductions in photoluminescence intensity at 24 h, revealing that the CHE-polyplexes induced protein expression at a very early stage after injection even under an in vivo condition.

Test Example B

1. Synthesis of PAsp(R/DET) with CHE Moieties at Substitution Degree of 60%

A PAsp(CHE/DET) with CHE moieties at a substitution degree of 60% in side chains was prepared by the simultaneous aminolysis reaction of PBLA with DET and 2-cyclohexylethylamine. PBLA (DP=28, 30 mg) was dissolved in NMP (2 mL) and cooled to 10° C. The PBLA solution was added dropwise to the mixture of DET (790 µL, 755 mg) and 2-cyclohexylethylamine (3.42 mL, 2.98 g) (molar ratio=1: 3.2). The resultant solution was stirred for 2 h at 10° C. under argon atmosphere. The reaction mixture was added dropwise to cold 5 M HCl (6 mL) for neutralization. The polymer product was purified by dialysis against 0.01 M HCl at 4° C. and then distilled water at 4° C. The dialyzed solution was lyophilized to obtain a solid powder. The obtained powder was dissolved in methanol (4 mL) with a small amount of triethylamine and then precipitated into an excess amount of diethyl ether to completely remove unreacted 2-cyclohexylethylamine. The precipitate was filtered and dissolved in distilled water. The polymer was further purified by dialysis against 0.01 M HCl at 4° C. and then distilled water at 4° C. The dialyzed solution was lyophilized to obtain the final product. Quantitative conversion of benzyl ester groups to DET moieties and CHE moieties in side chains was confirmed in the $^1$H NMR spectrum (10 mg/mL, 80° C.). As a result, it was found that the introduction numbers of DET moieties and CHE moieties were 12 and 16, respectively, and the substitution degree to CHE moieties was about 60%.

2. Preparation of mRNA-loaded Polyplexes using PAsp(CHE16/DET12)

The PAsp(CHE16/DET12) having CHE moieties at a substitution degree of 60% prepared in the section 1. was dissolved in 10 mM HEPES buffer (pH 7.3) and then mixed with in vitro transcribed (IVT) mRNA solution (100 ng/µL mRNA in 10 mM HEPES buffer, pH 7.3) to prepare polyplex solutions (20 ng/µL mRNA) at desired N/P ratios. As the mRNA, Gaussia luciferase (GLuc) mRNA was used.

3. mRNA Transfection using PAsp(CHE16/DET12) Polyplexes into Cultured Neuro-2A

Neuro-2A cells were seeded into a 96-well plate at a density of 8,000 cells/well in DMEM containing 10% FBS (DMEM/FBS). On the next day, the medium was replaced with fresh DMEM/FBS. The polyplex solutions prepared using GLuc mRNA were then added to each well (50 ng mRNA/well) and incubated for 24 h. The expression levels of GLuc were determined from the photoluminescence intensity of cell culture medium supernatants using the *Renilla* Luciferase Assay System for GLuc (Promega). The photoluminescence intensities were measured with a luminescence microplate reader (Mithras LB 940). In addition, as a control, the expression level of GLuc was determined in the same manner except that a polyplex of the PAsp(CHE11/DET15) with DP=26 and CHE moiety substitution degree=40% prepared in Test Example A and GLuc mRNA was used. The results are shown in FIG. 8.

As shown in FIG. 8, in each case of N/P ratio=3 or 5, the polyplex using the PAsp(CHE16/DET12) having CHE moieties at a substitution degree of 60% showed a remarkably higher photoluminescence intensity than the polyplex (N/P ratio=5) using the PAsp(CHE11/DET15) having CHE moieties at a substitution degree of 40%.

4. Preparation of mRNA-loaded Polyplex, sgRNA-loaded Polyplex, and mRNA/sgRNA-loaded Polyplex using PAsp(CHE16/DET12)

The PAsp(CHE16/DET12) was dissolved in 10 mM HEPES buffer (pH 7.3) and then mixed with IVT mRNA solution (100 ng/µL mRNA in 10 mM HEPES buffer, pH 7.3) or single-guide RNA (sgRNA) solution (100 ng/µL sgRNA in 10 mM HEPES buffer, pH 7.3) at N/P ratio=5 to prepare an mRNA-loaded polyplex and an sgRNA-loaded polyplex (20 ng/µL mRNA or sgRNA), respectively. In addition, IVT mRNA solution (100 ng/µL mRNA) and sgRNA solution (100 ng/µL sgRNA) were mixed in advance, and then mixed with a PAsp(CHE16/DET12) solution at N/P ratio=5 to prepare a polyplex simultaneously loaded with mRNA and sgRNA (mRNA/sgRNA-loaded polyplex). As the mRNA, SpCas9 mRNA was used.

5. In Vitro Genome Editing using PAsp(CHE16/DET12) Polyplexes

Primary hepatocytes were harvested from B6.Cg-Gt (ROSA)$_{26}$Sor$^{tm9(CAG-tdTomato)Hze}$/J mice (Ai9 mice, The Jackson Laboratory) and seeded in Vitronectin (A14700, ThermoFisher Scientific)-coated 8-well Lab-Tek™ chamber (Nalge Nunc International) at a density of 30,000 cells/well. Hepatocyte culture medium is DMEM11960 (Gibco) containing 10% FBS, 1% Penicillin-Streptomycin-Glutamine (10378-016, Gibco), 1% DMSO, and 1% supplement. The supplement (100x) is dexamethasone (0.392 g, 041-18861, Wako), insulin (5 mg, 096-03443, Wako), L-proline (0.3 g, 161-04602, Wako), nicotinamide (12.2 g, 141-01202, Wako), L-ascorbic acid 2-phosphate (0.58 g, A8960, Sigma), and human epidermal growth factor (100 μg, GPT10015L, Toyobo) in 100 mL pure water. The hepatocytes grew with the culture medium exchanged every other day. On the transfection day, the culture medium was replaced with fresh culture medium. Polyplex solutions prepared from SpCas9-mRNA and sgRNA (20 ng/μL mRNA or sgRNA, N/P=5) were then added to each well at varying concentrations and incubated for 48 h. In addition, as a control, genome editing was performed using LIPOFECTAMINE™ MessengerMAX (Invitrogen) loaded with SpCas9-mRNA and LIPOFECTAMINE™ RNAiMAX (Invitrogen) loaded with sgRNA. The incubated cells were subjected to fluorescence observation using a confocal laser scanning microscope (10× Apochromat) via excitation at 405 nm for Hoechst 33342 and excitation at 561 nm for tdTomato. The results are shown in FIG. 9. In this evaluation system, when genome editing is successful (specifically, when as illustrated in FIG. 10, double-strand cleavage occurs in a STOP cassette present upstream of the tdTomato gene), tdTomato is expressed. Therefore, the effect of genome editing is evaluated on the basis of a photoluminescence intensity derived from tdTomato.

As shown in FIGS. 9, fluorescence derived from tdTomato was observed in hepatocytes cotransfected with SpCas9 mRNA and sgRNA as polyplexes with PAsp (CHE16/DET12), revealing that the genome editing caused double-strand cleavage in the STOP cassette. In FIGS. 9A, the results of cotransfection with the SpCas9-mRNA-loaded polyplex and the sgRNA-loaded polyplex are shown. In FIGS. 9B, the results of transfection with the SpCas9-mRNA/sgRNA-loaded polyplex are shown.

6. In vivo Genome Editing using PAsp(CHE16/DET12) Polyplexes

A PAsp(CHE16/DET12) polyplex solution containing 1.5 μg SpCas9 mRNA and a PAsp(CHE16/DET12) polyplex solution containing 1.5 μg sgRNA were each prepared at N/P=5 in an amount of 5 μL. Two solutions were mixed immediately before administration, and then intracerebroventricularly administered to the 3rd ventricle of Ai9 mice. The brain was processed to tissue slices and observed by using ZEISS LSM 780 with a Plan-Apochromat 10x objective (Carl Zeiss). The genome editing in the brain was estimated from the fluorescence derived from tdTomato. The results are shown in FIG. 11($a$) and FIG. 11($b$).

As shown in FIG. 11($a$) and FIG. 11($b$), in the brain intracerebroventricularly injected with the PAsp(CHE16/DET12) polyplex containing SpCas9 mRNA and the PAsp (CHE16/DET12) polyplex containing sgRNA, fluorescence derived from tdTomato was observed, revealing that the intended genome editing occurred.

In addition, although fluorescence observation results are not shown, Ai9 mice were intramuscularly injected with a PAsp(CHE16/DET12) polyplex solution containing SpCas9 mRNA (N/P=5) and a PAsp(CHE16/DET12) polyplex solution containing sgRNA (N/P=5) in the same manner as described above, and as a result, fluorescence derived from tdTomato in a muscle tissue was observed, confirming that the intended genome editing occurred.

Test Example C

1. Synthesis of a Series of PAsp Derivatives bearing Various Hydrophobic Side Chains Various PAsp(R/DET)s (R: 2-cyclohexenylethyl (HEXEN), cyclohexylmethyl (CHM), 3-cyclopentylpropyl (CPP), and 3-cyclohexylpropyl (CHP)) were synthesized by slightly modifying the synthesis method for PAsp(CHE/DET). PBLA (DP=21) was dissolved in NMP (2 mL) and cooled to 5° C. The PBLA solution was added dropwise to the mixture of DET (CHE 530 μL, HEXEN 530 μL, CHM 440 μL, CPP 110 μL, CHP 96 μL) and the corresponding aliphatic amine (CHE 2300 μL, HEXEN 2300 μL, CHM 2130 μL, CPP 560 μL, CHP 560 μL) as summarized in Table 3. The resultant solution was stirred for 1 day at 5° C. under argon atmosphere. The reaction mixture was added dropwise to an excess amount of diethyl ether for precipitation. The precipitate was collected and dissolved in distilled water. The polymer product was purified by dialysis against 0.01 M HCl at 4° C. and then distilled water at 4° C. The dialyzed solution was lyophilized to obtain the final product. Quantitative conversion of benzyl ester groups to DET moieties and hydrophobic moieties in the side chains was confirmed in the $^1$H NMR spectrum (10 mg/mL, 80° C.). The reaction conditions and polymer compositions are shown in Table 3.

TABLE 3

| R | | PBLA (mg) | Molar ratio (DET: aliphatic amine) | DET (μL) | Aliphatic amine (μL) | Substitution degree of R (%) | Yield (%) |
| --- | --- | --- | --- | --- | --- | --- | --- |
| CHE: | (cyclohexyl-CH2CH2-*) | 20 | 1:3.2 | 530 | 2,300 | 55 | 31.6 |
| HEXEN: | (cyclohexenyl-CH2CH2-*) | 20 | 1:3.2 | 530 | 2,300 | 47 | 50.6 |

TABLE 3-continued

| R | | PBLA (mg) | Molar ratio (DET: aliphatic amine) | DET (μL) | Aliphatic amine (μL) | Substitution degree of R (%) | Yield (%) |
|---|---|---|---|---|---|---|---|
| CHM: | 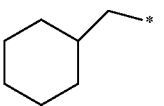 [SMILES: *CC1CCCCC1] | 20 | 1:4.0 | 440 | 2,130 | 49 | 56.2 |
| CPP: | 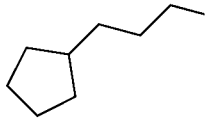 | 20 | 1:4.0 | 110 | 560 | 46 | 45.1 |
| CHP: | 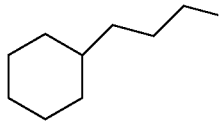 | 20 | 1:4.0 | 96 | 560 | 46 | 12.1 |

2. In Vitro mRNA Transfection using Various PAsp(R/DET) Derivatives

Jurkat cells were seeded into a 96-well plate at a density of 14,000 cells/well in RPMI containing 10% FBS (RPMI/FBS). At the same day, polyplex solutions prepared from GLuc mRNA and various PAsp(R/DET)s were added to each well (50 ng mRNA/well) and incubated for 48 h. The expression levels of GLuc were determined from the photoluminescence intensity of cell culture medium supernatants using the *Renilla Luciferase* Assay System for GLuc (manufactured by Promega). The photoluminescence intensities were measured with a luminescence microplate reader (Mithras LB 940). The results are shown in FIG. 12.

As shown in FIG. 12, in the case of using the polyplex formed from any of the PAsp(R/DET) derivatives, a photoluminescence intensity of more than 100,000 was obtained under the condition of N/P ratio=5, and a photoluminescence intensity of more than 10,000 was obtained even under the condition of N/P ratio=3. This reveals that each of those PAsp(R/DET) derivatives effectively functions as a carrier in the delivery of a nucleic acid, such as mRNA, into cells.

INDUSTRIAL APPLICABILITY

The amphiphilic poly(amino acid) of the present invention can be suitably used as a carrier in the delivery of a nucleic acid, such as mRNA, into cells.

The invention claimed is:

1. An amphiphilic poly(amino acid) represented by the following formula (1):

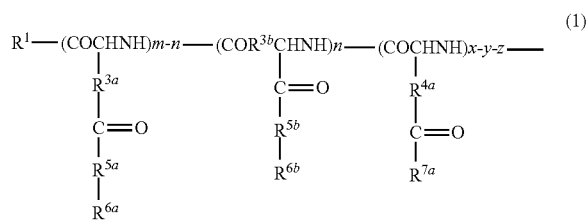

wherein:
  $R^1$ is a hydroxy group, an oxybenzyl group, an —O—$R^{1a}$ group, or an —NH—$R^{1b}$ group, wherein $R^{1a}$ and $R^{1b}$ are each independently an unsubstituted or substituted, linear or branched alkyl group having 1 to 12 carbon atoms;
  $R^2$ is a hydrogen atom, an unsubstituted or substituted, linear or branched alkyl group having 1 to 12 carbon atoms, or an unsubstituted or substituted, linear or branched alkylcarbonyl group having 1 to 24 carbon atoms;
  $R^{3a}$, $R^{3b}$, $R^{4a}$, and $R^{4b}$ are each independently a methylene group or an ethylene group;
  $R^{5a}$ and $R^{5b}$ are each independently —O— or —NH—;
  $R^{6a}$ and $R^{6b}$ are each independently an unsubstituted or substituted aliphatic hydrocarbon group having 7 to 12 carbon atoms that contains an alicycle;
  $R^{7a}$ and $R^{7b}$ are each independently:

—NH—(CH$_2$)$_{p1}$—[NH—(CH$_2$)$_{q1}$—]$_{r1}$NH$_2$   (i);

—NH—(CH$_2$)$_{p2}$—N[—(CH$_2$)$_{q2}$—NH$_2$]$_2$   (ii);

—NH—(CH$_2$)$_{p3}$—N{[—(CH$_2$)$_{q3}$—NH$_2$][—(CH$_2$)$_{q4}$—NH—]$_{r2}$H}   (iii);

or

—NH—(CH$_2$)$_{p4}$—N{—(CH$_2$)$_{q5}$—N[—(CH$_2$)$_{q6}$—NH$_2$]$_2$}$_2$   (iv), wherein p1 to p4, q1 to q6, and r1 and r2 are each independently an integer of from 1 to 5;
  $R^8$ is a side chain of an amino acid selected from the group consisting of ornithine, lysine, homolysine, arginine, homoarginine, and histidine;
  m is an integer of 9 or more;
  n is an integer of from 0 to m;
  x is an integer of from 2 to 300;

y is an integer of from 0 to x; and z is an integer of from 0 to x, provided that y+z≤x and 11≤m+x≤400, and repeating units in formula (1) can be randomly arranged.

2. The amphiphilic poly(amino acid) according to claim 1, wherein (m+x)×0.33≤m≤(m+x)×0.82.

3. The amphiphilic poly(amino acid) according to claim 1, wherein $R^{7a}$ and $R^{7b}$ are each independently —NH—$(CH_2)_{p1}$—[NH—$(CH_2)_{q1}$—]$_{r1}NH_2$.

4. The amphiphilic poly(amino acid) according to claim 1, wherein $R^{6a}$ and $R^{6b}$ are each independently a group of formula (2):

$$—R^{6c}—A(R^{6d})_{k2} \quad (2)$$

wherein,
wherein; $R^{6C}$ is an alkylene group having 1 to 7 carbon atoms,
$R^{6d}$ is an alkyl group having 1 to 3 carbon atoms,
A is a cycloalkyl ring or cycloalkenyl ring having 3 to 9 carbon atoms, and k2 is an integer of from 0 to 2, provided that the number of carbon atoms in the group of the formula (2) is within the range of from 7 to 12.

5. The amphiphilic poly(amino acid) according to claim 4, wherein $R^{6c}$ is an ethylene group, a propylene group, or a butylene group.

6. The amphiphilic poly(amino acid) according to claim 4, wherein $R^{6a}$ and $R^{6b}$ are each independently a cyclooctylethyl group, a cycloheptylmethyl group, a cycloheptylethyl group, a cyclohexylmethyl group, a cyclohexylethyl group, a cyclohexylpropyl group, a cyclohexylbutyl group, a cyclopentylethyl group, a cyclopentylpropyl group, a cyclopentylbutyl group, a cyclopentylpentyl group, a cyclobutylpropyl group, a cyclobutylbutyl group, a cyclobutylpentyl group, a cyclopropylbutyl group, a cyclopropylpentyl group, a cyclopropylhexyl group, a 1-cyclohexene-1-ethyl group, a 2-cyclohexene-1-ethyl group, or a 3-cyclohexene-1-ethyl group.

7. A complex comprising:
the amphiphilic poly(amino acid) of claim 1 and
a nucleic acid.

8. The complex according to claim 7, further comprising a protein.

9. The complex according to claim 7, wherein the nucleic acid is selected from the group consisting of a messenger ribonucleic acid (mRNA), a plasmid deoxyribonucleic acid (DNA), a donor DNA, a single guide ribonucleic acid (sgRNA), clustered regularly interspaced short palindromic repeats ribonucleic acid (crRNA), small interfering ribonucleic acid (siRNA), a micro ribonucleic acid (RNA), a short hairpin ribonucleic acid (shRNA), an antisense nucleic acid, a decoy nucleic acid, an aptamer, or a ribozyme.

10. A complex comprising:
the amphiphilic poly(amino acid) of claim 1 and
a protein.

11. An amphiphilic poly(amino acid) represented by the following formula (1'):

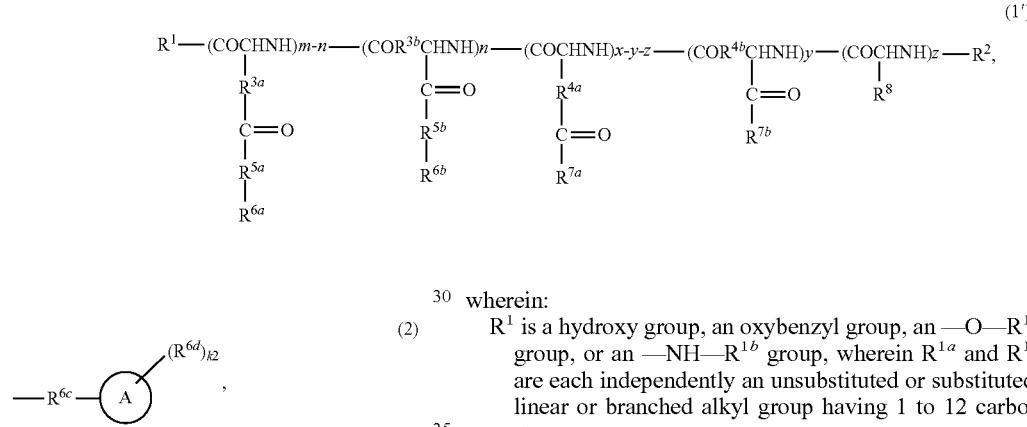

wherein:
$R^1$ is a hydroxy group, an oxybenzyl group, an —O—$R^{1a}$ group, or an —NH—$R^{1b}$ group, wherein $R^{1a}$ and $R^{1b}$ are each independently an unsubstituted or substituted, linear or branched alkyl group having 1 to 12 carbon atoms;

$R^2$ is a hydrogen atom, an unsubstituted or substituted, linear or branched alkyl group having 1 to 12 carbon atoms, or an unsubstituted or substituted, linear or branched alkylcarbonyl group having 1 to 24 carbon atoms;

$R^{3a}$, $R^{3b}$, $R^{4a}$, and $R^{4b}$ are each independently a methylene group or an ethylene group;

$R^{5a}$ and $R^{5b}$ are each independently —O— or —NH—;

$R^{6a}$ and $R^{6b}$ are each independently an unsubstituted or substituted aliphatic hydrocarbon group having 7 to 12 carbon atoms that contains an alicycle;

$R^{7a}$ and $R^{7b}$ are each independently:

—NH—$(CH_2)_{p1}$—[NH—$(CH_2)_{q1}$—]$_{r1}$NH$_2$     (i);

—NH—$(CH_2)_{p2}$—N[—$(CH_2)_{q2}$—NH$_2$]$_2$     (ii);

—NH—$(CH_2)_{p3}$—N{[—$(CH_2)_{q3}$—NH$_2$] [—$(CH_2)_{q4}$—NH—]$_{r2}$H}     (iii);

or

—NH—$(CH_2)_{p4}$—N{—$(CH_2)_{q5}$—N[—$(CH_2)_{q6}$—NH$_2$]$_2$}$_2$     (iv), wherein p1 to p4, q1 to q6, and r1 and r2 are each independently an integer of from 1 to 5;

$R^8$ is a side chain of an amino acid selected from the group consisting of ornithine, lysine, homolysine, arginine, homoarginine, and histidine;

m and x are integers, wherein (m+x)×0.33 m (m+x)×0.82 and 11 m+x 400;

n is an integer of from 0 to m;

y is an integer of from 0 to x; and z is an integer of from 0 to x, provided that y+z≤x, and repeating units in formula (1') can be randomly arranged.

12. The amphiphilic poly(amino acid) according to claim 11, wherein the m is an integer of 5 or more.

13. The amphiphilic poly(amino acid) according to claim 11, wherein $R^{7a}$ and $R^{7b}$ are each independently —NH—$(CH_2)_{p1}$—[NH—$(CH_2)_{q1}$—]$_{r1}$NH$_2$.

14. The amphiphilic poly(amino acid) according to claim 11, wherein $R^{6a}$ and $R^{6b}$ are each independently a group of formula (2):

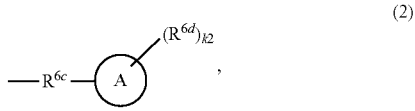

(2)

wherein, $R^{6c}$ is an alkylene group having 1 to 7 carbon atoms, $R^{6d}$ is an alkyl group having 1 to 3 carbon atoms, A is a cycloalkyl ring or cycloalkenyl ring having 3 to 9 carbon atoms, and k2 is an integer of from 0 to 2, provided that the number of carbon atoms in the group of the formula (2) is within the range of from 7 to 12.

15. The amphiphilic poly(amino acid) according to claim 14, wherein $R^{6c}$ is an ethylene group, a propylene group, or a butylene group.

16. The amphiphilic poly(amino acid) according to claim 14, wherein $R^{6a}$ and $R^{6b}$ are each independently a cyclooctylethyl group, a cycloheptylmethyl group, a cycloheptylethyl group, a cyclohexylmethyl group, a cyclohexylethyl group, a cyclohexylpropyl group, a cyclohexylbutyl group, a cyclopentylethyl group, a cyclopentylpropyl group, a cyclopentylbutyl group, a cyclopentylpentyl group, a cyclobutylpropyl group, a cyclobutylbutyl group, a cyclobutylpentyl group, a cyclopropylbutyl group, a cyclopropylpentyl group, a cyclopropylhexyl group, a 1-cyclohexene-1-ethyl group, a 2-cyclohexene-1-ethyl group, or a 3-cyclohexene-1-ethyl group.

* * * * *